United States Patent
Avnir et al.

(10) Patent No.: US 9,463,245 B2
(45) Date of Patent: Oct. 11, 2016

(54) ENTRAPMENT OF BIOACTIVES IN SOL-GEL ALUMINA MATERIALS

(71) Applicant: Yissum Research Development Company of the Hebrew University of Jerusalem Ltd., Jerusalem (IL)

(72) Inventors: David Avnir, Jerusalem (IL); Abraham Rutenberg, Haifa (IL); Vladimir V. Vinogradov, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 14/267,425

(22) Filed: May 1, 2014

(65) Prior Publication Data
US 2014/0328907 A1    Nov. 6, 2014

Related U.S. Application Data

(60) Provisional application No. 61/818,730, filed on May 2, 2013.

(51) Int. Cl.
| | |
|---|---|
| *A61K 47/02* | (2006.01) |
| *A61K 38/46* | (2006.01) |
| *A61K 9/00* | (2006.01) |
| *A61K 9/14* | (2006.01) |
| *A61K 9/16* | (2006.01) |
| *A61K 38/00* | (2006.01) |

(52) U.S. Cl.
CPC ............ *A61K 47/02* (2013.01); *A61K 9/0019* (2013.01); *A61K 9/143* (2013.01); *A61K 9/1611* (2013.01); *A61K 38/465* (2013.01); *C12Y 301/01007* (2013.01); *A61K 38/00* (2013.01)

(58) Field of Classification Search
CPC ........... A61K 39/00; A61K 47/48238; A61K 47/48907; A61K 47/48915; A61K 9/5123; A61K 9/5153; A61K 9/5192; A61K 2039/53; A61K 31/7105; A61K 31/711; A61K 38/16; A61K 48/00; A61K 48/0058; B82Y 5/00
USPC ...... 514/1.1, 44 R, 44 A, 178, 182; 435/325, 435/375; 424/184.1, 422, 450, 484
See application file for complete search history.

(56) References Cited

PUBLICATIONS

Xu et al., "Synthesis of mesoporous alumina with highly thermal stability using glucose template in aqueous system", Microporous and Mesoporous Materials, vol. 91, pp. 293-295, (2006).

Liu et al., "Probing Trace Phenols Based on Mediator-Free Alumina Sol-Gel-Derived Tyrosinase Biosensor", Anal. Chem., vol. 72, pp. 4707-4712, (2000).

Liu et al., "Al2O3 sol-gel derived amperometric biosensor for glucose", Analytica Chimica Acta, vol. 392, pp. 135-141, (1999).

Yağar et al., ",Non-covalent immobilization of quince (Cydonia oblonga) polyphenol oxidase on alumina", Acta Chimica Slovenica, vol. 49, Issue 4, p. 893, (2002).

Amoura et al., "Sol-gel encapsulation of cells is not limited to silica: long-term viability of bacteria in alumina matrices", Chem. Commun., pp. 4015-4017 (2007).

Yoldas, "Hydrolysis of Aluminium Alkoxides and Bayerite Conversion", J. appl. Chem. Biotechnol., vol. 23, pp. 803-809, (1973).

Yoldas, "A Transparent Porous Alumina", Ame. Cer. Soc. Bul., vol. 54, No. 3, pp. 286-288, (1975).

Yoldas, "Alumina Sol Preparation from Alkoxides", Ame. Cer. Soc. Bul., vol. 54, No. 3, pp. 289-290, (1975).

Yoldas, "Preparation of glasses and ceramics from metal-organic compounds", Journal of Materials Science, vol. 12, pp. 1203-1208, (1977).

Yoldas, "Hydrolytic Polycondensation of Si(OC2H5)4 and Effect of Reaction Parameters", Journal of Non-Crystalline Solids, vol. 83, pp. 375-390, (1986).

DeLuca et al., "Parenteral Drug-Delivery Systems", Pharmaceutics and Pharmacy Practice, Chapter 8, pp. 238-250, J.B. Lippincott Co., Philadelphia, Pa., Banker and Chalmers, eds., (1982).

Trissel, "Intravenous Infusion Solutions", pp. 622-630, ASHP Handbook on Injectable Drugs, 4th ed., (1986).

Rutenberg et al., "Synthesis and enhanced thermal stability of albumins@alumina: towards injectable sol-gel materials", Chem. Commun., vol. 49, pp. 5636-5638, (2013).

Podbielska et al., "Sol-gel technology for biomedical engineering", Bulletin of the Polish Academy of Sciences: Technical Sciences, vol. 53, No. 3, pp. 261-271, (2005).

Vlad-Oros et al., "Bioorganically Doped Sol-Gel Materials Containing Amyloglucosidase Activity", APTEFF, vol. 37, pp. 1-192, (2006); BIBLID: 1450-7188 (2006); vol. 37, pp. 179-186.

Coradin et al., "Sol-gel Chemistry in Medicinal Science", Current Medicinal Chemistry, vol. 13, No. 1, pp. 1-10, (2006).

*Primary Examiner* — Janet Epps-Smith

(74) *Attorney, Agent, or Firm* — Vorys, Sater, Seymour & Pease LLP

(57) ABSTRACT

Provided is a platform for entrapment within alumina sol-gel carriers of labile biologically active materials such as proteins, therapeutic enzymes, enzymes of industrial relevance, antigens, and small molecules for achieving successful and efficient protective storage, protection from harsh environmental conditions such as heat, pH and chemicals, delivery to site and subsequent treatment and/or vaccination against diseases against which the active agents are targeted.

16 Claims, 19 Drawing Sheets

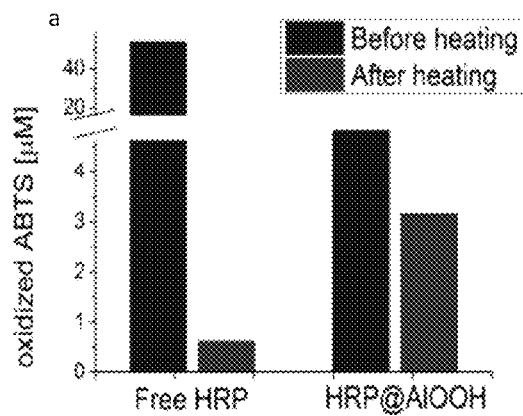
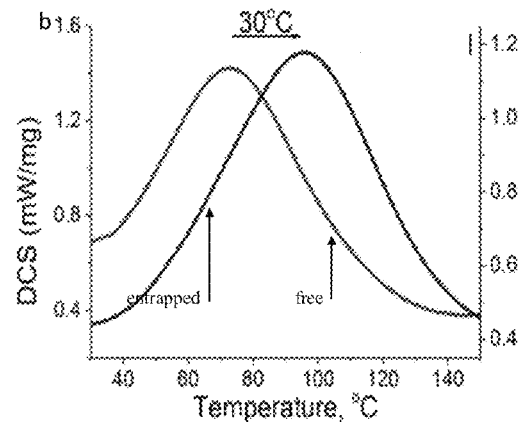
Fig. 15A                    Fig. 15B
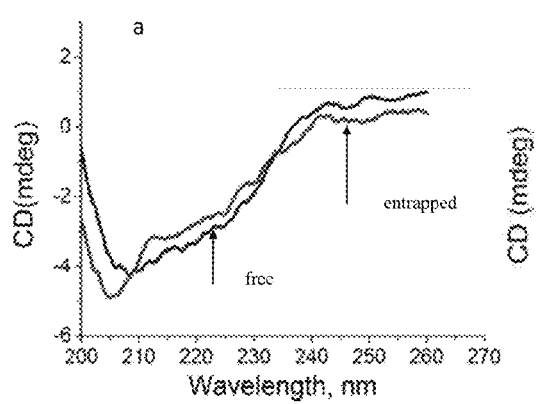
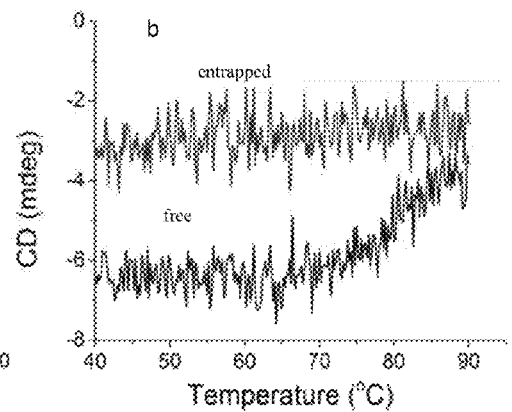
Fig. 16A                    Fig. 16B

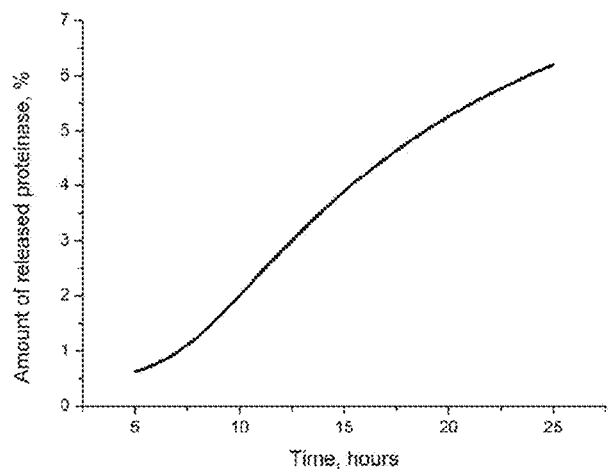
Fig. 20B
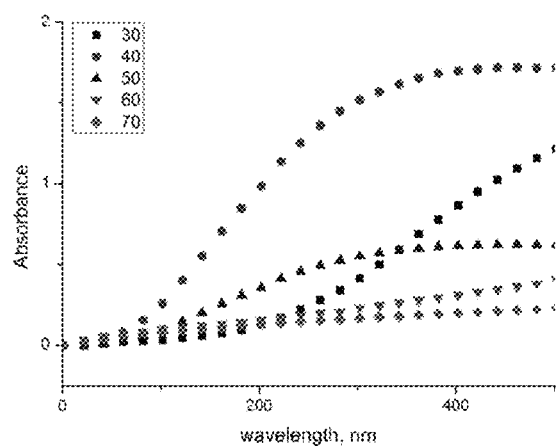
Fig. 21A
Fig. 21B
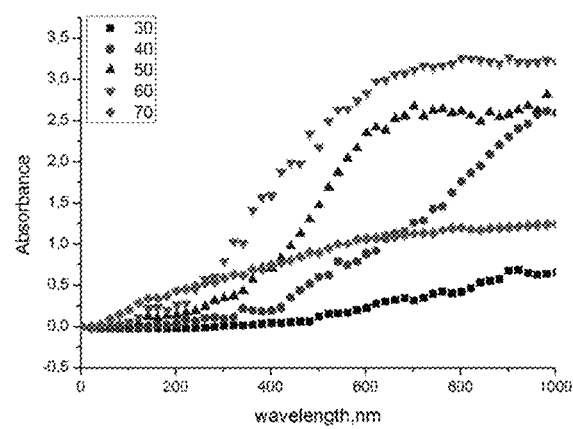

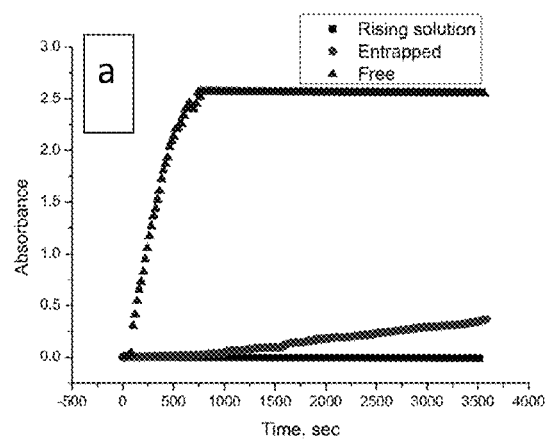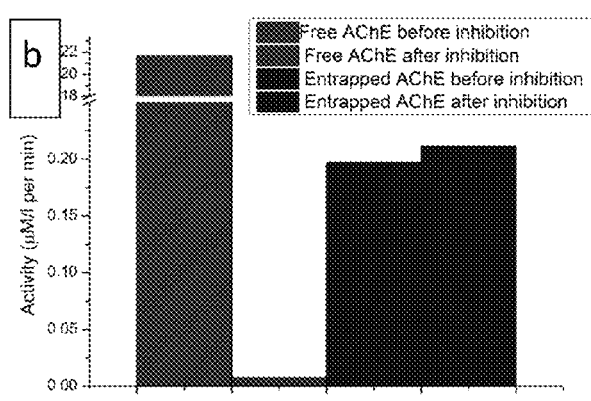
Fig. 27A    Fig. 27B
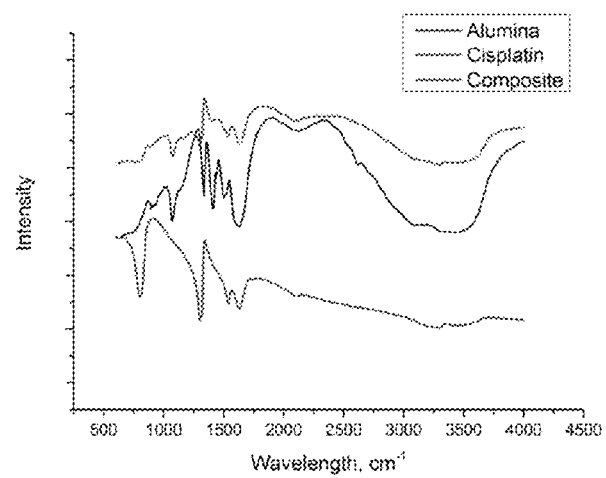
Fig. 28

ENTRAPMENT OF BIOACTIVES IN SOL-GEL ALUMINA MATERIALS

FIELD OF THE INVENTION

The invention generally provides novel materials capable of entrapping and delivering biological agents and method of preparation and application.

BACKGROUND OF THE INVENTION

Common difficulties associated with use of bioactive materials in a variety of industries are mainly based on loss of activity with time or with decomposition or inactivation upon contact with one or more environmental conditions such as hear and chemicals. The difficulties are greater where the bioactive material is intended for biomedical or therapeutic applications. Destruction or inactivation of the bioactive en route to site of disease is a particular difficulty where enzymes are concerned.

One of methods of protection which have been used extensively involves encapsulation of the bioactive in a material matrix which protects the bioactive from heat, light, oxygen as well as from decomposition when in contact with biological entities within the human body.

Alumina is the only metal oxide which is currently approved for injection to a human subject. Organic and bio-organic doping of alumina sol-gel is much less developed than the corresponding silica-based chemistry, but examples for entrapment of small molecules [1] and of enzymes [2-4], and E. coli [5], exist.

BACKGROUND ART

1. B. Xu, B. Xiao, Z. Yan, X. Sun, J. Sloan, S. L. Gonzalez-Cortes, F. Alshahrani, M. L. H. Green, *Micropor and Mesopor Mat,* 2006, 91, 293.
2. Z. J. Liu, B. H. Liu, J. L. Kong, J. Q. Deng, *Anal Chem,* 2000, 72, 4707.
3. Z. Liu, B. Liu, M. Zhang, J. Kong, J. Deng, *Anal Chim Acta,* 1999, 392, 135.
4. H. Yağar, A. Sağiroğlu, *Acta Chim Slov,* 2002, 49, 893.
5. M. Amoura, N. Nassif, C. Roux, J. Livage, T. Coradin, *Chem Commun,* 2007, 4015.

SUMMARY OF THE INVENTION

The inventors of the invention disclosed herein have developed a unique and novel platform for entrapment within alumina sol-gel carriers of labile biologically active materials such as proteins, therapeutic enzymes, enzymes of industrial relevance, antigens, and small molecules for achieving successful and efficient protective storage, protection from harsh environmental conditions such as heat, pH and chemicals, delivery to site and subsequent treatment and/or vaccination against diseases against which the active agents are targeted.

The inventors demonstrate herein that not only that the alumina sol-gel carrier materials exhibit characteristics similar to alumina used in vaccines, but also that the entrapment of bioactives, within the alumina materials enhances their thermal stability significantly, as compared with the corresponding silica sol-gel materials, which makes the alumina sol-gel materials a promising novel and unexpected venue for delivery of drug entities.

Thus, generally the present invention concerns alumina sol-gel materials and pharmaceutical compositions comprising same, the materials comprising labile pharmaceutically active agents, as disclosed, entrapped in the alumina sol-gel material. The material and compositions comprising same may be adapted for various administration modes and may specifically be adapted for injection.

In a first aspect of the invention, there is provided a material in the form of a plurality of alumina sol-gel particles, the particles comprising at least one labile bioactive agent, the material being suitable for use in medicine. In other words, the material is a pharmaceutical material.

The invention further provides alumina sol-gel materials comprising at least one labile bioactive agent.

Further provided is a hybrid material comprising at least one labile bioactive agent, wherein said bioactive agent being contained, entrapped or enclosed by alumina sol-gel particles.

For the sake of brevity, the hybrid of alumina sol-gel and bioactive agent materials is referred to herein, in short, as "bioactive@alumina". For example, where the bioactive is a protein, the hybrid material of the invention may be referred to in short as "protein@alumina"

As will be further explained and demonstrated hereinbelow, the at least one labile bioactive agent is contained, entrapped, enclosed or held within enclosures or pores or cavities within the alumina sol-gel material. The sol-gel material may alternatively be regarded as a coating formed around the labile bioactive agent. During the preparation of the bioactive@alumina, the sol-gel coats or forms around the bioactive agent, forming one or more cavities that contain or hold the bioactive. The ability of the bioactive agent to leak from the alumina material by e.g., diffusion or by initial partial or full destruction of the alumina coating, is further demonstrated hereinbelow and may be used to tailor controlled-release, e.g., sustained-release or slow-release materials, as further contemplated below.

The sol-gel process typically involves conversion of monomers into a "sol", namely a colloidal solution which thereafter is converted into an integrated network, the "gel" in the form of discrete particles or network polymers.

Appropriate metal alkoxides are typically mixed with water and a mutual solvent to form a solution. Hydrolysis leads to the formation of intermediate species which subsequently condensate to produce metal-O-metal (wherein the metal is Si or metals such as Al) bonds. The gel formed leads to a rigid, three-dimensional network which is characterized by a plurality of submicron pores and polymeric chains. Once the solvent liquid is removed resulting material is known as a xerogel. Heat treatment of the xerogel produces viscous sintering and effectively transforms the gel into a dense glass.

The alumina sol-gel material employed in accordance with the invention as encapsulating, entrapping or matrix material for holding the at least one labile bioactive agent are based on aluminum oxide, alumina, materials selected from any of the alumina known crystalline forms. The preparation of the alumina sol-gel is described hereinbelow. Additional methods of preparation of alumina sol-gel are known in the art, see for example: Yoldas et al., J. Appl. Chem. Biochem, 23, 803-9, 1973; Yoldas et al., Ame. Cer. Soc. Bul., 54, 286-8, 1975; Yoldas et al., Ame. Cer. Soc. Bul., 54, 289-90, 1975; Yoldas et al., J. Matr. Sci., 12, 1203-8, 1977; and Yoldas et al., J. non-Crys. Sol., 83, 375-90, 1986.

The alumina sol gel may be in the form of an amorphous material or in the form of randomly sized and shaped particles. In some embodiments, the particles are characterized by an average size in the sub-micron to micron range. In some embodiments, the average size is between 0.1 and 50 micron. In some embodiments, the size of the particles is between 0.1 and 40 microns, between 0.1 and 30 microns, between 0.1 and 20 microns, between 0.1 and 10 microns, between 1 and 50 microns, between 1 and 40 microns, between 1 and 30 microns, between 1 and 20 microns, between 1 and 10 microns, between 1 and 9 microns, between 1 and 8 microns, between 1 and 7 microns, between 1 and 6 microns, between 1 and 5 microns, between 1 and 4 microns, or between 1 and 3 microns.

In some embodiments, the particles are characterized by an average size of 1, 2, 3, 4, 5, 6, 7, 8, 9 or 10 microns.

The invention further provides at least one labile bioactive agent entrapped, encapsulated or contained within alumina sol-gel material, i.e., bioactive@alumina.

The at least one "labile bioactive agent" is typically an active agent approved by health authorities for the treatment and/or diagnosis of a disease state in a subject. The bioactive may have a medical or veterinary therapeutic, prophylactic or diagnostic utility. The bioactive agent, may be a biological origin and may be selected from a variety of molecules ranging from small organic molecules either synthetically produced or from a natural source, and other biologicals, to high molecular weight biological molecules such as proteins, enzymes, peptides, antibodies, nucleic acids (DNA and RNA), growth factors, cells (bacteria, stem cells), viruses and carriers (plasmids).

In some embodiments, the bioactive agent is selected from such which undergo in vivo one or more of chemical interaction, physicochemical interaction, an action on an infectious agent, and any other interaction with an entity present in vivo or a cell or an organ. Such agents may be used in accordance with the invention in one or more in vivo or in vitro (or ex vivo) utilities.

In some embodiments, the bioactive agent may be selected from therapeutic agents suitable for curing and/or relieving, partially or fully, symptoms associated with a disease or disorder and prophylactic agents suitable for preventing occurrence or re-occurrence of a disease or disorder or.

In some embodiments, the bioactive agent is selected from peptides, proteins such as hormones, enzymes, antibodies, receptor binding proteins, antibody fragments, antibody conjugates, nucleic acids such as aptamers, iRNA, siRNA, microRNA, DNA, RNA, antisense nucleic acid or the like, antisense nucleic acid and the like, VEGF inhibitors, macrocyclic lactones, dopamine agonists, dopamine antagonists, low-molecular weight compounds, high-molecular-weight compounds, and conjugated bioactive agents.

In some embodiments, the bioactive agent is selected from androgen inhibitors, polysaccharides, growth factors, hormones, anti-angiogenesis factors, peptides, polypeptides, proteins, amino acids, hormones, interferons and cytokines.

In some embodiments, the bioactive agent is selected from immunomodulators such as cytokines, interleukins, interferon, colony stimulating factor, tumor necrosis factor, and others.

In some embodiments, the bioactive agent is selected amongst such materials used in cosmetics for topical application on a skin region.

In some embodiments, the bioactive agent is selected from prodrugs, bio-imaging agents such as radioactive and florescent agents. Alternatively, the bioactive agent is selected amongst such having biological activity and thus may be used to treat, diagnose, cure, mitigate, prevent, ameliorate, and/or modulate a disease or disorder.

The bioactive agents contained, entrapped or enclosed by the alumina sol-gel materials are said to be labile. The term "labile" refers within the context of the recited bioactive to any lability/sensitivity that could cause the bioactive to degrade, denaturtae, decompose, unfold, undergo deactivation, undergo denaturation, lose of tertiary structure, undergo bond dissociation or bond re-forming, exposure of cryptic domains, and others. The sensitivity may be to any one of heat, light, pH (acid lability or base lability), hydrolysis, enzymes, certain physiological environment, oxidation, and solvents.

In some embodiments, the bioactive agent is heat-sensitive.

In some embodiments, the bioactive agent is acid-sensitive or base-sensitive.

In some embodiments, the bioactive material is selected amongst heat-sensitive materials such as heat-sensitive peptides, proteins such as hormones, enzymes, antibodies, receptor binding proteins, antibody fragments, antibody conjugates, nucleic acids such as aptamers, iRNA, siRNA, microRNA, DNA, RNA, antisense nucleic acid or the like, antisense nucleic acid and the like, VEGF inhibitors, macrocyclic lactones, dopamine agonists, dopamine antagonists, low-molecular weight compounds, high-molecular-weight compounds and conjugated bioactive agents.

In some embodiments, the heat-sensitive bioactive material is selected from androgen inhibitors, polysaccharides, growth factors, hormones, anti-angiogenesis factors, peptides, polypeptides, proteins, amino acids, hormones, interferons and cytokines.

In some embodiments, the heat-sensitive bioactive material is selected from immunomodulators such as cytokines, interleukins, interferon, colony stimulating factor, tumor necrosis factor and others.

In some embodiments, the at least one labile, e.g., heat-sensitive, bioactive is an enzyme, a peptide, a polypeptide, a protein or an amino acid.

In some embodiments, the at least one labile heat-sensitive bioactive is an enzyme. The enzyme may be selected amongst industrial enzymes and therapeutic enzymes.

In some embodiments, the at least one labile heat-sensitive bioactive is not an enzyme.

Where enzymes are the bioactive agent(s) in bioactive@alumina according to the invention, the enzyme employed may be selected amongst such used medical applications, for example, for release of toxic drugs in vivo from their pro-drugs; for the treatment of enzyme deficiency diseases; or for starving cancerous cells by depletion of essential biochemicals they cannot produce.

Thus, the enzyme may be selected from peroxidases, phosphatases, alkaline phosphatase, asparaginases, DNAzymes, NADH dehydrogenases, protease, lipase, amylase, cellulose, hydrolases, oxidoreductases, transferases, lyases, isomerases, hexose oxidase, glucose oxidase, alcohol dehydrogenase (ADH), microperoxidase, myoglobin, alpha-amylase, chloroperoxidase, alpha-chymotrypsin, horseradish peroxidase, laccase, manganese peroxidase, soybean peroxidase, trypsin, glycosylase, lysozyme and any combination thereof.

The invention further provides a pharmaceutical composition comprising alumina sol-gel particles, the particles comprising at least one labile bioactive agent. The invention further provides bioactive@alumina as herein described.

In some embodiments, the composition may comprise a mixture or a plurality of different alumina sol-gel particles. The differences between the particles may be in at least one of size, shape, constitution, the specific labile bioactive contained therein, the concentration of the bioactive, the conditions of preparation and so forth. In some embodiments, the composition may comprise at least one carrier, adjuvant or diluents suitable and appropriate for the specific intended administration mode. The at least one carrier, adjuvant or diluents may be selected to arrest, hasten or control release of the bioactive agent from the alumina material, may be selected to adapt the composition for the intended use, may be selected to enable better suspension or dispersion characteristics of the bioactive@alumina in the composition medium, etc.

The choice of carrier, adjuvant or diluents will be determined in part by the particular bioactive@alumina, as well as by the particular method used to administer the bioactive@alumina or a composition comprising same. Accordingly, there is a wide variety of suitable formulations of the pharmaceutical composition of the present invention. The following formulations for oral, aerosol, parenteral, subcutaneous, intravenous, intramuscular, interperitoneal, rectal and vaginal administration are merely exemplary and are in no way limiting.

Formulations suitable for oral administration can consist of (a) liquid solutions or suspensions in diluents, such as water, saline, or orange juice; (b) capsules, sachets, tablets, lozenges, and troches, each containing a predetermined amount of the bioactive@alumina, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the bioactive@alumina in a flavor, usually sucrose and acacia or tragacanth, as well as pastilles comprising the bioactive@alumina in an inert base, such as gelatin and glycerin, or sucrose and acacia, emulsions, gels, and the like containing, in addition to the bioactive@alumina, such carriers as are known in the art.

The bioactive@alumina of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. The bioactive@alumina can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

The parenteral formulations typically contain from about 0.5 to about 25% by weight of bioactive@alumina in solution. Suitable preservatives and buffers can be used in such formulations. In order to minimize or eliminate irritation at the site of injection, such compositions may contain one or more nonionic surfactants. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The bioactive@alumina of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, $4^{th}$ ed., pages 622-630 (1986).

Additionally, the bioactive@alumina of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

In other embodiments, the composition may comprise at least one additional active or non-active agent, which may be contained within the bioactive@alumina hybrid material or in the composition, yet outside of the bioactive@alumina hybrid (namely in combination with the bioactive@alumina).

In other embodiments, the composition may comprise at least one additional active or non-active agent, which may be contained within the bioactive@alumina hybrid material and an additional amount of the same or different active or non-active agent which may be outside of the bioactive@alumina hybrid (namely in combination with the bioactive@alumina).

The at least one additional active agent may be selected amongst antiviral agents, antimicrobial agents, anti-infective agents, antibiotics, antifungal agents, anticancer agents, analgesics, corticosteroids, steroids, agents for topical uses, ophthalmic agents, antioxidants and any other agent depending on the intended use.

The at least one additional non-active agent may be selected from surface active agents, dispersing agents, granulating and disintegrating agents, binding agents, lubricating agents, sweetening agents, flavoring agents, coloring agents, preservatives, suspending agents, dispersing or wetting agents, emulsifying agents, buffers, thickening agents, fillers, stabilizing agents and any other suitable agent known in the art.

As the examples provided below demonstrate, the alumina may be tailored to hold or contain the bioactive to achieve prolonged or short-term encapsulation. Additionally the alumina may be tailored to achieve any release profile necessary by varying one or more of alumina type, concentration of bioactive, ratio of alumina to bioactive, and by varying a plurality of procedure conditions. As such, the bioactive@alumina of the invention may be used for (a) non-release encapsulation of the bioactive, e.g., therapeutic and industrial enzymes for containing without permitting release or leakage of the bioactive therefrom; (b) release of bioactive agents of low molecular weight or reduced interactions with the alumina matrix; and/or (c) release in a controlled manner of the bioactive agent(s).

The invention thus provides a broad spectrum of release profiles of bioactives from the alumina matrix. In one related aspect, the invention provides a slow-release hybrid bioactive@alumina according to the invention. As used herein, the term "slow-release" refers to the hybrid material bioactive@alumina, wherein the bioactive agent is released from the alumina (and subsequently delivered to a site of interest) for a sustained period of time. In some embodiments, the release of the bioactive agent is over several days, several weeks or longer.

Similarly, the invention provides a fast-release hybrid bioactive@alumina according to the invention. As used herein, the term "fast-release" refers to the hybrid material or to a formulation or composition comprising same, wherein the bioactive agent is released from the bioactive@alumina at a rate of >10%, >20%, >30%, >40%, >50%, >60% or >70% of the alumina contents over a period of 1, 2, 3 or 4 days.

The hybrid material of the invention or compositions comprising same may also be tailored as sustained release formulations or compositions. As used herein, the term "sustained release" refers to release of the bioactive from the bioactive@alumina material at a profile that conforms to a release rate over a specific period of time. In some embodiments, the sustained release formulations of the invention are formed where the bioactive has a short half-life or, e.g., require active blood plasma levels for long periods of time.

The invention further provide a "drug delivery" platform for delivering at least one bioactive to a target organ, tissue or cell in vivo or ex vivo, wherein the bioactive is sensitive to at least one agent, element or environment, and is carried, contained, entrapped or held in alumina sol-gel material, as disclosed herein.

The invention also provides a platform for entrapping, without spontaneous short-term or long-term release of bioactive agents, wherein the release may take place upon application of an external means, e.g., biological, chemical or physical which trigger or allow controlled, immediate, slow or sustained release of the bioactive therefrom by inducing leakage, diffusion, alumina decomposition or any other means by which the bioactive agent can release from the alumina. Such a characteristic of the invention permits maintaining or increasing the stability of a bioactive for prolonged periods of time, e.g., days, weeks, months and longer, as compared to the typically exhibited stability of the same bioactive when not encapsulated in a bioactive@alumina system of the invention.

The results presented herein below demonstrate that the stability of bioactive agents, such as enzymes, have increased dramatically when in a bioactive@alumina system of the invention, with their shelf-life, release profile, stability to heat and other harsh environmental conditions and therefore functionality and activity maintained or even more so favorably affected.

In another aspect, the invention provides a methodology for prolonging shelf-life of a bioactive during storage, delivery or use, by arresting bioactive decomposition, decreasing or diminishing bioactive sensitivity, increasing or maintaining stability of a bioactive, protecting a bioactive from increased sensitivity or lability, as defined herein, or for achieving enhanced functionality of a bioactive, the method comprising contacting said bioactive under conditions permitting entrapment of said bioactive in an alumina sol-gel.

The invention also provides a method for achieving delivery of a bioactive agent to a disease site without having said bioactive degrade or deactivate en route to site, the method comprising forming a bioactive@alumina in accordance with the invention and administering said bioactive@alumina or a composition comprising same, in accordance with the invention.

In another aspect, the invention provides a method for achieving an enhanced delivery of a bioactive agent to a disease site, the method comprising administering a bioactive@alumina or a composition comprising same, in accordance with the invention.

In a further aspect, the invention provides a method for achieving an enhanced delivery of a bioactive to a body organ or tissue, the method comprising administering a bioactive@alumina or a composition comprising same, in accordance with the invention.

The invention further provides a method of treatment of a disease or disorder in a subject, said method comprising administering to said subject a pharmaceutical composition according to the invention. In some embodiments, the bioactive is released from the bioactive@alumina adhering to a fast, slow or sustained release profile.

The compositions of the invention comprising the bioactive@alumina may be administered to a subject in need thereof for achieving treatment or prevention of a disease state or disorder. The disease or disorder may by any such disease or disorder against which the bioactive is directed. In some embodiments, the disease is selected from viral, microbial, infective, fungal, proliferative, cancer, inflammation, disease of the eyes, skin diseases and others.

The amount of the bioactive in the alumina and/or the effective amount the bioactive@alumina in the administered composition may be determined by such considerations as may be known in the art. The amount must be effective to achieve the desired therapeutic effect, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the rate of release of the bioactive from the alumina, the affinity of the ligand to the receptor, its distribution profile within the body, a variety of pharmacological parameters such as half life in the body, undesired side effects, if any, factors such as age and gender, and other considerations known to the medical practitioner.

The bioactive@alumina or compositions comprising same are effective in treatment regimens. In other words, the bioactive@alumina is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease from occurring or a combination of two or more of the above.

The treatment regimen may include administration of several divided dosages, staggered dosages administered daily or sequentially, continuous infusion, or bolus injection, each of which may be proportionally increased or decreased.

The bioactive@alumina according to the invention or a composition comprising same may comprise an amount of the bioactive sufficient to deliver the bioactive in an amount between 1 mg to about 1,000 mg, about 20 mg to about 950 mg, about 40 mg to about 900 mg, about 75 mg to about 850 mg, about 150 mg to about 750 mg, about 200 mg to about 700 mg, about 300 mg to about 600 mg, about 500 mg to about 600 mg, about 1 mg to about 300 mg, about 1 mg to about 250 mg, about 2 mg to about 200 mg, about 2 mg to about 150 mg, about 5 mg to about 100 mg, about 7 mg to about 900 mg, about 10 mg to about 80 mg, about 25 mg to about 75 mg, about 30 mg to about 60 mg, about 40 mg to about 50 mg, daily, twice daily or at any other regimen, to the subject being treated (human or non-human).

The bioactive@alumina of the invention may further be utilized as agents suitable for diagnosis. Thus, the invention further provides method of diagnosis comprising administering a diagnostically effective amount of a bioactive@alumina according to the invention.

The invention further provides a process for endowing thermal stability for a heat-sensitive bioactive, the process comprising reacting the heat-sensitive bioactive material with an ultrasonically prepared alumina sol to afford a hybrid material of alumina sol-gel entrapping, containing or holding said heat-sensitive bioactive, the hybrid material being heat-stable.

As demonstrated herein, the thermal stability of the bioactive when entrapped within the alumina sol-gel material is evident from the increase in the temperature under which the bioactive undergoes decomposition or inactivation as defined hereinabove. In some embodiments, the thermal stability is defined by an increase in the temperature of at least 10° C.; namely, the temperature causing decomposition or inactivation of the bioactive in bioactive@alumina is 10° C. greater as compared to the temperature under which the bioactive alone undergoes decomposition or inactivation. In some embodiments, the temperature different is at least 15° C., at least 20° C., at least 25° C., at least 30° C., at least 35° C., at least 40° C., at least 45° C., at least 50° C., at least 55° C., at least 60° C., at least 65° C., at least 70° C. or at least 75° C., at least 80° C., at least 85° C., at least 90° C., at least 95° C., at least 100° C., at least 150° C., at least 200° C., at least 250° C., at least 300° C., at least 350° C., at least 400° C., at least 450° C. or at least 500° C.

In some embodiments, the temperature different is between 10 and 15° C., between 10 and 20° C., between 10 and 25° C., between 10 and 30° C., between 10 and 35° C., between 10 and 40° C., between 10 and 45° C., between 10 and 50° C., between 10 and 55° C., between 10 and 60° C., between 10 and 65° C., between 10 and 70° C., between 10 and 75° C., between 10 and 80° C., between 10 and 85° C., between 10 and 90° C., between 10 and 95° C., between 10 and 100° C., between 10 and 150° C., between 10 and 200° C., between 10 and 250° C., between 10 and 300° C., between 10 and 350° C., between 10 and 400° C., between 10 and 450° C. or between 10 and 500° C.

In some embodiments, the temperature different is between 100 and 150° C., between 100 and 200° C., between 100 and 250° C., between 100 and 300° C., between 100 and 350° C., between 100 and 400° C., between 100 and 450° C. or between 100 and 500° C.

Thus, in a hybrid material according to the invention, comprising alumina sol-gel and at least one heat-sensitive bioactive material, the at least one heat sensitive bioactive material being entrapped within the alumina sol-gel material exhibits a deactivation temperature (namely, a temperature at which the bioactive agent decomposes, degrades, undergoes inactivation or any other destructive process, as defined herein) at least 10° C. higher as compared to the same heat sensitive bioactive material when free, namely when not entrapped in accordance with the invention.

For the various utilities of the invention, the bioactive@alumina may be packaged as a commercial package or a kit optionally comprising, in addition to the bioactive@alumina, at least one carrier or diluents for formulating the bioactive@alumina into a desired formulation. The commercial package or kit may also comprise instructions of use.

The invention further provides a method for preparation of an alumina sol-gel material, said material being in the form of alumina sol-gel particles comprising at least one labile bioactive. To avoid heat degradation or altering other properties like physical and biological properties of bioactive agents, the disclosed processes utilize methods that do not involve the use of heat. The method for preparation of an alumina sol-gel material according to the invention comprises preparing alumina sol under ultrasonic conditions and treating said sol with at least one labile bioactive agent under conditions permitting entrapping of the bioactive within the sol-gel formed.

In some embodiments, the method is carried out under neutral conditions.

In some embodiments, the treating of the sol with the at least one labile bioactive agent is carried out at room temperature.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 10A—The enzymatic reaction rates of AcP@Alumina as a function of pNPP concentration. FIG. 10B—An Eadie-Hofstee plot of the AcP@alumina dose-response data. FIG. 10C—HR-SEM image of AcP@alumina.

FIG. 11A: The enzymatic activity of AcP@alumina at different temperatures in the range of 20-75° C. FIG. 11B: The thermal stability of entrapped AcP: Activity along heating-cooling cycles (heating: 1 hour, 60 0C).

FIG. 3B Ellipticity monitored at the 215 nm helical peak.

FIGS. 15A-B provide FIG. 15A-HRP catalyzed formation of oxidized ABTS after 10 min, comparing free and entrapped HRP incubated at 37° C. or 75° C. FIG. 15B-DSC analysis: An increase of 30° C. in the denaturation temperature to 100° C. is observed for HRP@alumina (right curve), compared with free HRP (left curve).

FIGS. 16A-B provide FIG. 16A-Circular dichroism spectra of HRP in a freshly made solution and of HRP entrapped within alumina. FIG. 16B-Ellipticity monitored at the 205 nm helical peak.

FIG. 17A: Asparaginase catalyzed formation of ammonia after 30 min, comparing free and entrapped ASP incubated at 37° C. or 75° C. FIG. 17B: Ellipticity monitored at the 220 nm helical peak.

FIGS. 20A-B show the morphology of the final PRTNS@alumina composite, which are densely packed.

FIGS. 21A-D shoes the enzymatic activity of free (FIG. 21A) and entrapped (FIG. 21B) PRTNS at different temperatures between 30-700 C. FIG. 21C-Relative activity of free and entrapped PRTNS. FIG. 21D—The thermal stability of entrapped PRTNS: Activity along heating-cooling cycles.

FIG. 22B-Specific activity at 30.0° C. of PRTNS entrapped at four different concentrations in alumina monolith. FIG. 22C-Fit correction of the composite activity at different enzyme concentration.

FIG. 24A: Relative activity of free and entrapped XLNS at different temperatures FIG. 24B: DSC analysis: An increase of 30° C. in the denaturation temperature is observed for XLNS@alumina (right curve), compared with free XLNS (left curve).

FIG. 25A-Circular dichroism spectra of XLNS in a freshly made solution and of HRP entrapped within alumina. FIG. 25B-Ellipticity monitored at the 205 nm helical peak.

FIGS. 27A-B provide: FIG. 27A—The activity of free and entrapped AChE during the time. FIG. 27B-Activity of free and entrapped AChE before and after inhibition test with aluminum chloride.

FIG. 28 shows FTIR spectra of the pure alumina, cisplatin, and their composite FIG. 29 provides XRD diffractograms of cisplatin@alumina.

DETAILED DESCRIPTION

Figure 1:
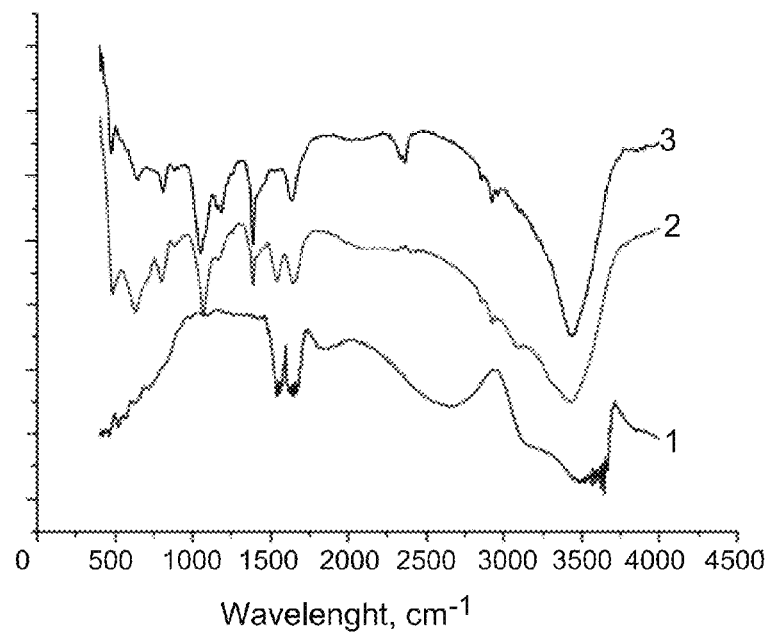
FIG. 1 shows FTIR spectra of the pure HSA (1), pure alumina-IV (3) and HSA@ alumina-IV.
Figure 2:
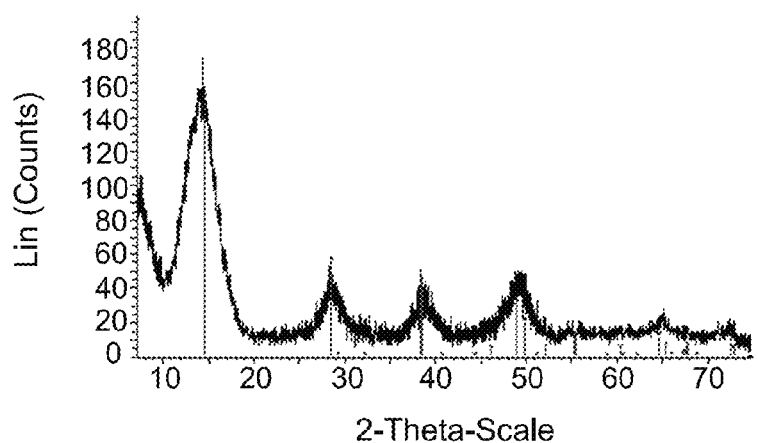
FIG. 2 shows XRD diffractograms of OVA@alumina-I. (The vertical lines are the literature XRD peaks for Boehmite (JCPDS file No. 21-1307).

The present invention concerns alumina sol-gel materials comprising a labile pharmaceutically active agent, such as peptides, proteins such as hormones, enzymes, antibodies, receptor binding proteins, antibody fragments, antibody conjugates, nucleic acids such as aptamers, iRNA, siRNA, microRNA, DNA, RNA, antisense nucleic acid or the like, antisense nucleic acid and the like, VEGF inhibitors, macrocyclic lactones, dopamine agonists, dopamine antagonists, low-molecular weight compounds, high-molecular-weight compounds, and conjugated bioactive agents.

In the following, the uniqueness of the invention is demonstrated by exemplary biological models.

The composite bioactive@alumina were prepared as particles in the size range of 1-10 microns, similar to the particle size of alumina adsorbed/precipitated vaccines. The alumina used may be any one of the 6 alumina composites known. In the exemplary models provided herein, the alumina was polycristalline boehmite (gamma-alumina, AlO(OH)) which is the bio-active form of alumina used in commercial aluminum hydroxide adsorbed vaccines. The crystalline form was verified using XRD for both undoped and doped alumina.

Estimation of the amount of entrapped bioactive, e.g., protein was done by TGA analysis, UV spectrophotometry at 280 nm and the Micro-Bradford assay (595 nm). The highest load of entrapped protein tested was 27% by weight, as this is the upper limit of antigen given per immunization in conventional alumina adsorbed vaccines (25 ug antigen per 25 ug $Al^{3+}$).

All measurements indicated a nearly quantitative entrapment of the protein. Higher antigen/alumina ratios were also possible, and this may be useful in light of the limitations on the amount of aluminum per dose (USA: 0.85 mg/dose, Europe: 1.25 mg/dose).

Chemicals

Aluminum isopropoxide, acid phosphatase (AcP, cat. No. P-0157), asparaginase (ASP, cat. No. A-0884), horseradish peroxidase (HRP, cat. No P-8375), L-asparagine, Nessler's reagent, trichloroacetic acid, ammonium sulfate, p-nitrophenyl phosphate (pNPP), 2,2'-Azino-bis(3-ethylbenzothiazoline-6-sulfonic acid) (ABTS), hydrogen peroxide 30% were all obtained from Sigma-Aldrich. Glycine buffers were prepared from glycine solutions (0.05M; from Sigma-Aldrich) with desired volumes of 1.0 M NaOH or 1.0 M HCl.

Sol-Gel Synthesis of Alumina

Ultrasonic (US) energy source was used to prepare alumina sol at neutral pH. In detail, 2.2 g of $Al(C_3H_7O)_3$ was added to 50 mL of deionized water at 90° C. and a white precipitate was formed immediately. Before US treatment, the precipitate was kept at 90° C. under vigorous stirring for 15 min to complete the production of boehmite nanoparticles and to complete the evaporation of the isopropanol formed during hydrolysis. The final suspension was ultrasonically treated (Elma S 10H 37 kHz, 30 W) for 2 h. After 2 h a viscous sol was formed. The resulting sol was cooled to room temperature. The dried matrix had a surface area of 153 m2/g, pore volume of 0.097 $cm^3$/g and an average pore size of ~2.5 nm.

Entrapment of the Proteins in Alumina:

A non-limiting example of bioactives in accordance with the invention is proteins.

As model proteins, three proteins of the albumin family were used: Ovalbumin (OVA), bovine serum albumin (BSA) and human serum albumin (HSA). Various entrapment procedures were used, denoted hereinbelow as I, II, III and IV.

Method I: As a first step, Boehmite sol was prepared as follows: 2.837 g Al(i-Pro)$_3$ was hydrolyzed for 45 min in 51 ml DDW at 85° C. in an air-open flask. Then, 1.67 ml HCl 1M was added and temperature was increased to 95° C. to catalyze the peptization. The flask was kept air-open for additional 3 hrs to enable isopropanol evaporation, and then placed under reflux for additional 16 hours. Then, the reflux was removed and the water was allowed to evaporate by air-exposure until the total sol volume was reduced to less than 25 ml, which was then re-adjusted to 25 ml with DDW (15 mg $Al^{3+}$/ml sol) (alumina-I).

The second step—the protein entrapment—was carried out as follows: 45.4 mg OVA grade V was dissolved in 42 ml 25 mM L-histidine buffer at pH=6.91. 4.0 ml of the protein-buffer solution was added to 1.0 ml of alumina sol, vortexed and left for 1 h under shaking in ice. Then 100 µl of NaF 50 mg/ml solution was added to the 5.0 ml protein-sol under vortex. The solution became immediately turbid and the gel forms. The tube was centrifugated for 10 min at 5,000 rpm and placed at 4° C. for 10 days for gel aging. The supernatant was then removed and the tube placed in a desiccator under vacuum for 3-7 days for xerogel formation, until the gel has shrunk to about 10% its initial volume (OVA@alumina-I). The above ratios yielded a 7.2 µg OVA/ 25 ng $Al^{3+}$ composite, which was approximately 10% OVA dopant by weight.

Methods II and III: The second and third methods used Yoldas procedures by peptizing aluminum hydroxide precipitate in acids: acetic acid (alumina-II) or nitric acid (alumina-III). In detail, 3.28 g of $Al(C_3H_7O)_3$ was added to 50 ml of deionized water and a white precipitate was formed immediately. The precipitate was peptized with 0.2 mL of concentrated nitric acid or with 2.0 mL for acetic acid at 90° C. under vigorous stirring for 2 h (also to evaporate the isopropanol formed during hydrolysis) to produce stable transparent boehmite sols, (6.7 mg and 6. 5 mg Al3+/ml sol, respectively). The pH of the final solution was 2.8 (4.8 in acetic media).

The second step—the albumin entrapment—was carried out un-buffered by dissolving 0.03 g of the protein (BSA and HSA within alumina-II and alumina-III respectively) in 20.0 mL boehmite sol at room temperature. The suspension was aged for 3 h and dried at 20° C. for a week. TGA analyses indicated a ~8 w/w % loading in the two samples.

Method IV: This method (alumina-IV) followed method II but without any acid or buffer. The white precipitate was ultrasonically treated (37 kHz, 0.063 kW) for 4 h (final pH=7.3). After 4 h a viscous sol was formed.

The second step—the albumin entrapment—was carried out at room temperature by dissolving 0.03 g of the protein in 20.0 mL of the sol (alumina-IV): with BSA—BSA@alumina-IV, or with HSA—HSA@alumina-IV. The suspension was treated as above resulting in a ~8 w/w % loading.

Albumins and Vaccines

In the following, protein@alumina was prepared (e.g., BSA@alumina-IV), where the protein was OVA, BSA or HSA, and methods were (as detailed in the Experimental Section below): I—catalysis with NaF, II—peptization with acetic acid, III-peptization with nitic acid, and IV—ultrasonic preparation at neutral pH.

It should be noted that the use of acetic acid and particularly of ultrasonic treatment provide solution pH values of 4.8 and 7.3, respectively, that are suitable for biomolecules and corresponds to an optimum range at which the albumin molecules and the particles have opposite charges, providing the needed electrostatic interaction for entrapment.

For verifying the entrapment of the proteins within the alumina sol-gel, the thermal behavior was tested, as described below, together with analyzing the organic-bioorganic hybrid materials under IR spectroscopy (FTIR), which clearly showed a superposition of the typical absorption bands of the matrix and the biological dopant. A representative example—HSA@alumina-IV—is shown in FIG. 1, wherein the IR spectrum of the composite—line 2 was indeed a superposition of the spectra of HSA (line 1) and alumina (line 3).

Figure 3A:
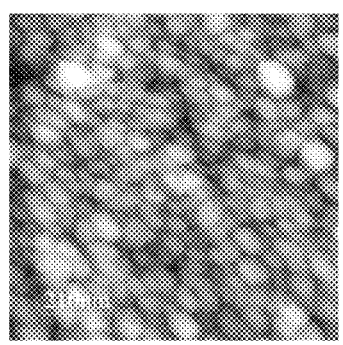
FIGS. 3A-C presents two (FIG. 3A) and three-dimensional (FIG. 3B) AFM images of the HSA@alumina-II and (FIG. 3C) its particle size distribution.
Figure 3B:
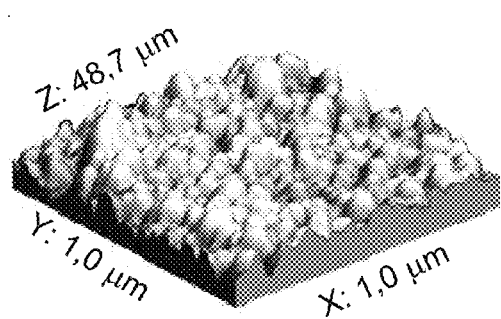
Figure 3C:
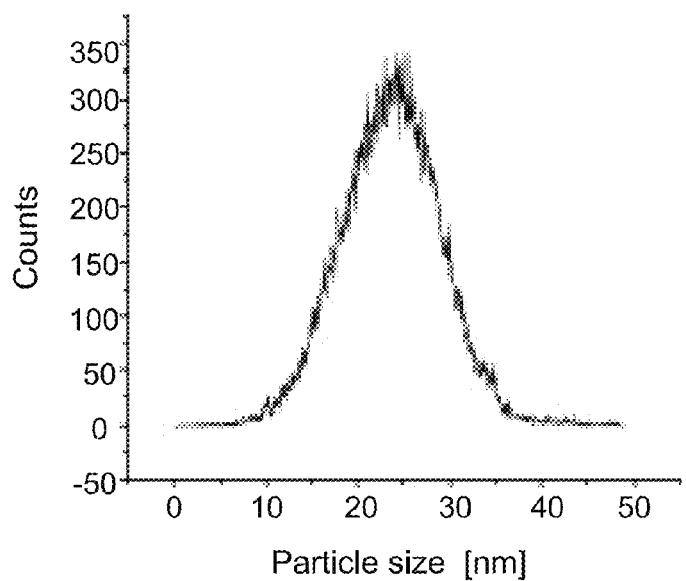

AFM pictures in the semi-contact mode of the dried samples reveal the aggregation of these elementary particles into larger particles of several tens of nm, as shown for instance for HSA@alumina-II (FIG. 3; as expected, DLS data provided larger hydrodynamic sizes).

Surface area and porosity analyses (by nitrogen adsorption, analyzed by the BET and BJH equations) confirmed typical microporosity, with some induced changes due to protein entrapment. The values before protein entrapment were: surface area of 246 $m^2$/gr, pore volume of 0.23 $cm^3$/gr and pore size of ~4 nm, with an increase, while the surface area values after entrapment were 370 and 356 m$^2$/gr for BSA and HSA, respectively, with an increase the pore volume to 0.34 cm$^3$/gr for both proteins, and with a little change in the average pore size. It seems that the effect of the protein was to interfere with the aggregation, resulting in a more open structure.

The thermal stability of proteins was a very strict limitation of their use for various medical and industrial applications, often requiring refrigeration. The use of alumina makes this potential stabilization even more relevant and interesting.

The stability studies have been carried out by differential scanning calorimetry (DSC). DSC has been traditionally used for the follow-up of phase transitions within materials, and is less known to determine phase transitions in proteins due to the denaturation process. Indeed, proteins demonstrate a DSC peak (either the original curve or its second derivative) upon heating.

Figure 4:
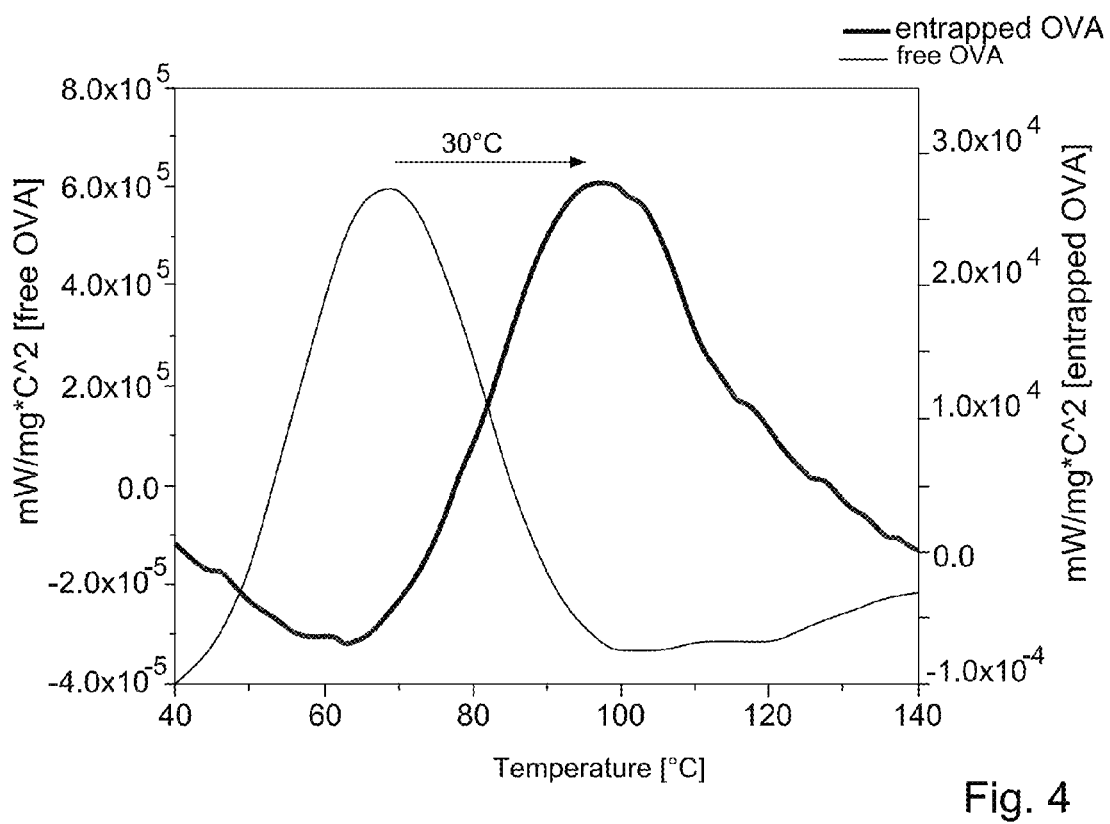
FIG. 4 presents DSC analyses of free and entrapped BSA (left) and free and entrapped HAS (right): 1-protein@alumina-III, 2-protein@alumina-II, 3-protein@alumina-IV.

As shown in FIG. 4, the denaturation temperature of OVA was shifted by 30 degrees when entrapped by method I after three days of aging and reached 100° C., an extremely high temperature for denaturation. Similar stabilization was observed for BSA@alumina-II and III (FIG. 4).

Figure 5A:
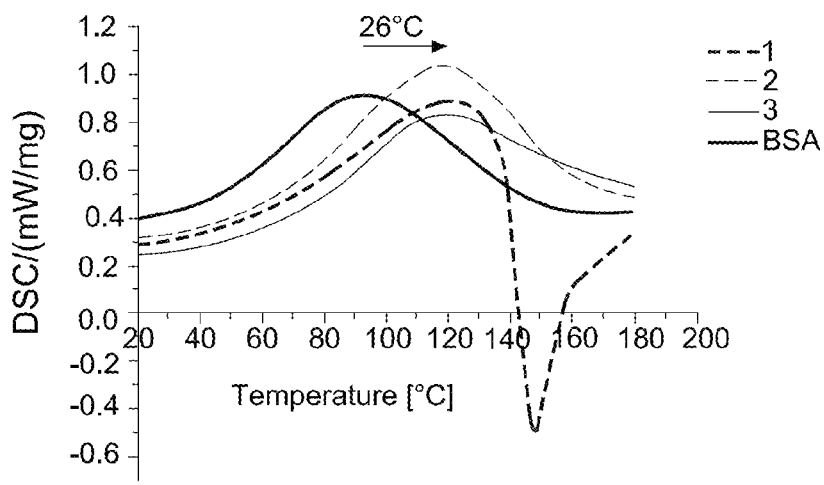
FIGS. 5A-B present gradual increase in stabilization with aging of OVA entrapped in alumina-gel-I.
Figure 5B:
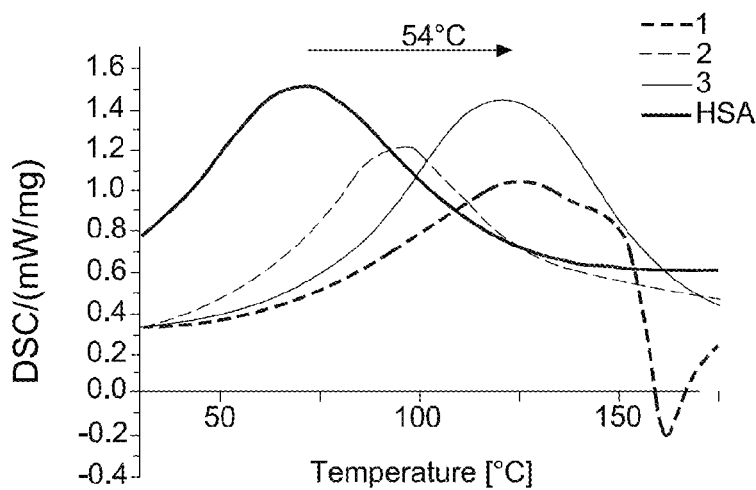

An exceptionally high stabilization was obtained for HSA in HSA@alumina-IV: an increase of 54° C. to the denaturation temperature of 120° C. (!) (FIG. 5B), highlighting that the ultrasonic sol-treatment utilized in accordance with the invention, was optimal for bioactives such as proteins.

Figure 6:
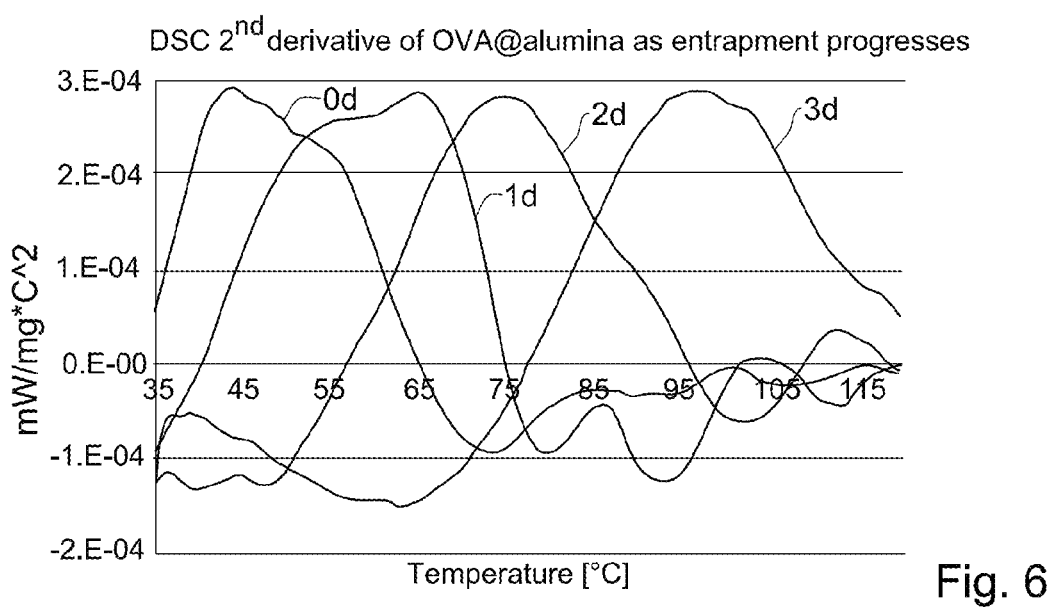
FIG. 6 presents 2nd derivative of the DSC curves of FIG. 5.

FIG. 6 shows yet another feature of the stabilization by entrapment in alumina: the stabilization of OVA progresses with time of aging of the doped alumina-gel (Method I). When no time was allocated for xerogel transformation (0 days), the peak mean was only at ~47° C. One day of xerogel transformation, and the peak mean value shifted towards 60° C. Two days and the mean value reached 75° C. Three days and it peaked at 100° C.

Thus, the method and materials of the invention may be regarded protein-friendly for entrapment of bioactives such as proteins. Trapped in alumina, such materials exhibited marked stabilization and thus opened a potential door for sol-gel materials to be considered as carriers of bioactive molecules.

Injectable Proteins@Alumina and Conditions for Release Measured by Immunogenic Activity In-vivo experiments in BALB/c mice have demonstrated high levels of specific antibody titer against a model antigen—ovalbumin—entrapped in alumina, following immunization by injection. No side effects have been observed for the duration of the experiment (months), supporting the safety of the composite vaccines.

Some unique properties of the immune response have been observed. These include a significant IgM titer 31 days following vaccination suggesting that the antigen was being released from the composite antigen-adjuvant matrix one month after administration; and an extremely high antigen specific IgG titer was observed 67 days following vaccination (an end-point titer of 1:51, 200, with no boost). This resembled the titer obtained by adjuvants which are far stronger than alumina—Freund's complete adjuvant, or three immunizations with conventional alumina adsorbed vaccines, obtained here by only a single immunization with the composite alumina entrapped vaccine.

Controlled release of the antigen during a prolonged period of time may provide gradually and continually exposure of the recipient's immune system. This may yield improved and longer-term immunological memory. In fact, the immune response may be optimized by tailoring the desired release rate. Another considerable benefit may be the reduction of the number of required vaccinations to obtain an adequate immunological memory. The use of an alumina adjuvant as a releasing matrix, adds unique features, as explained above.

Dozens of vaccine adjuvants which have been disqualified due to excess potency when inoculated directly (e.g. FCA) may be reassessed under controlled release conditions when entrapped within a sol-gel matrix.

One of the aforementioned benefits of the entrapment process is the gradual, controlled release rate. Spectrophotometric Micro-Bradford assay, known as a sensitive assay to determine protein concentrations, was used to evaluate the amount of released protein from alumina entrapped gels, compared to desorption, following 12 days of incubation at ambient temperature with various concentrations of phosphate buffer. The results (Table 1) clearly show that the entrapped protein was released much slower as compared to the desorption of adsorbed protein. It should be stressed that while control of release from the adsorbed state was an almost impossible task, the rate of protein release from the entrapped matrix could be controlled by changing parameters of the sol-gel process (e.g. longer aging time; in this experiment the gels were aged for only 1 day).

TABLE 1

| Adsorbed | | | | Entrapped | | | |
|---|---|---|---|---|---|---|---|
| Phosphate [mM] | O.D. 595 nm | OVA conc. [mg/ml] | % Released Protein | Phosphate [mM] | O.D. 595 nm | OVA conc. [mg/ml] | % Released Protein |
| 100 | 0.1726 | 0.051 | 97.0 | 100 | 0.1144 | 0.033 | 62.0 |
| 80 | 0.1703 | 0.050 | 95.5 | 80 | 0.1242 | 0.036 | 67.7 |
| 60 | 0.1705 | 0.050 | 95.7 | 60 | 0.1131 | 0.032 | 61.2 |
| 40 | 0.1443 | 0.042 | 79.6 | 40 | 0.1092 | 0.031 | 58.9 |
| 20 | 0.1140 | 0.032 | 61.7 | 20 | 0.0707 | 0.020 | 37.3 |
| 10 | 0.0699 | 0.019 | 36.9 | 10 | 0.0036 | 0.001 | 1.8 |

10 weeks old BALB/c mice were immunized with the alumina entrapped vaccines. In order to evaluate the vaccines safety, the mice were physically examined and weighed 3 times a week in the first month following vaccination by a veterinary or a veterinary technician. After the first month, physical examination+weighing were carried out twice a week. It should be noted that the ethical committee conditioned any further testing of the vaccines in larger population of mice by demonstrating first that they were safe in a small group of mice. Throughout 50 days following immunization no side effects were observed. 3 days following immunization the vaccines were completely absorbed and the mice did not show any signs of pain when touching the injection site. As can be seen in FIG. 8, there was a general trend of increase in all mice weight vs. time following immunization. The bleedings on days 13 and 31 were marked, usually followed by a small decrease in weight. Bleedings (100 ul) were taken from the submandibular vein before immunization (day 0), on day 13, on day 31 and on day 67 following vaccination. Sera were obtained from blood and analyzed for IgM and IgG OVA specific titer in comparison to day 0 of the same mouse. All sera were kept at 4° C. until analysis.

Figure 7A:
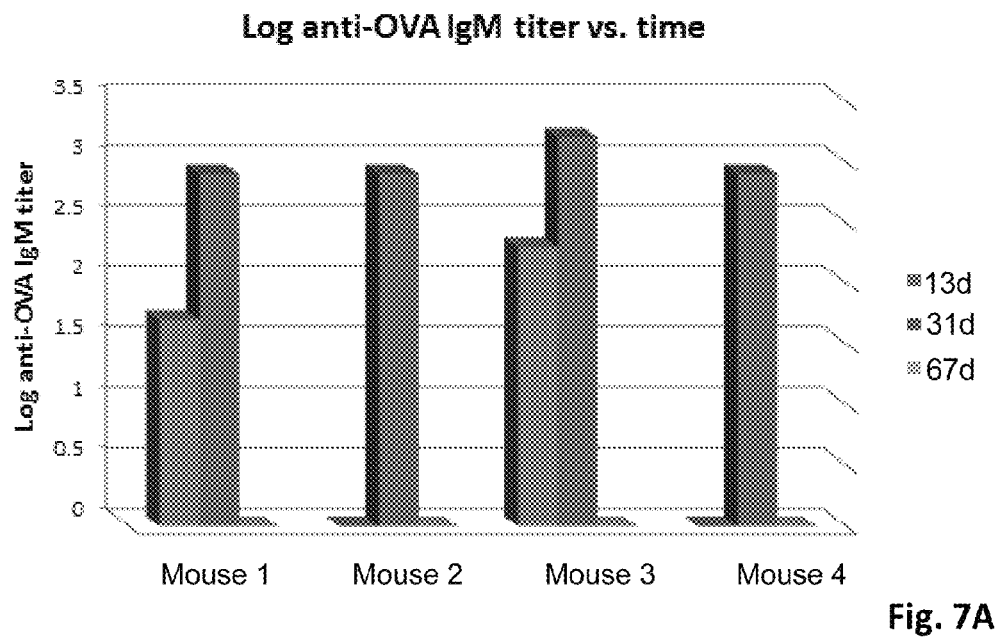
FIGS. 7A-B present Log anti-OVA antibody titer vs. time following immunization for each mouse (Note that each column stands for a different composition or preparation method).
Figure 7B:
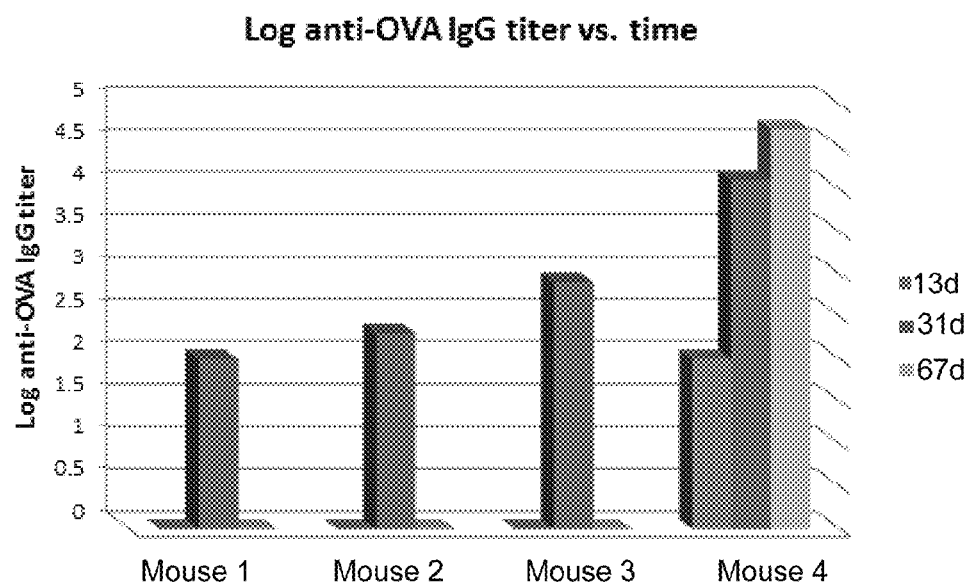
Figure 8:
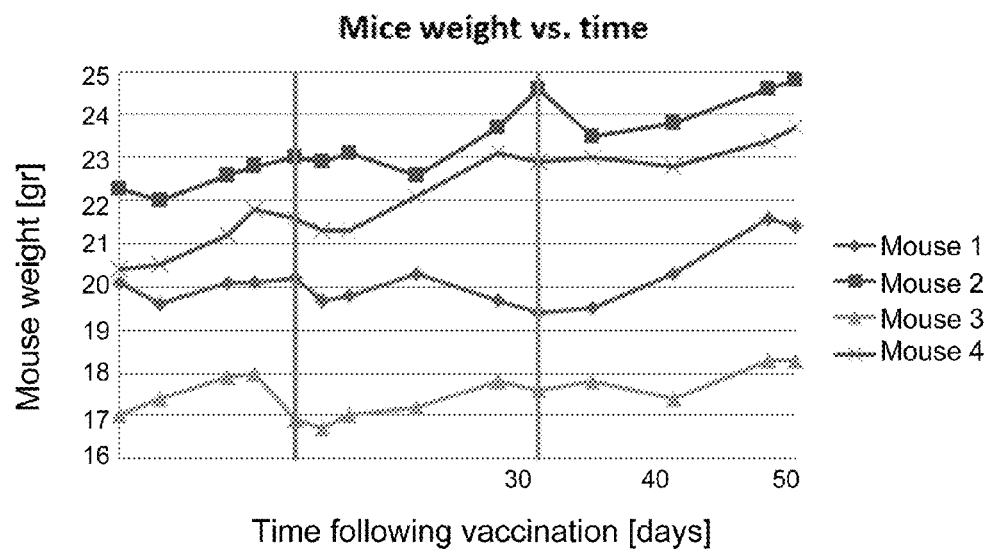
FIG. 8 shows mice weight vs. time following vaccination.

FIG. 7 clearly demonstrates that anti-OVA specific titer was obtained in all mice, both IgM and IgG, thus proving the concept that alumina entrapped vaccines work.

Enzymes within Alumina

For the entrapment of AcP, a mixture of 50 µl, of glycine-HCl buffer solution (pH 4.5) and 1500 µL, of freshly prepared alumina sol was transferred to a cuvette and then 40 µL, of AcP (200 U/mL) was added. Ten minutes later the sol was left in vacuum desiccator at room temperature for 24 hours. The AcP@alumina (0.009% by weight for the kinetics studies and 0.1% for the CD and DSC measurements) was rinsed inside final polystyrene cuvette with 1.0 mL of glycine solution (pH 4.5) to assure removal of any adsorbed protein. The entrapment of HRP within alumina (0.05%) was carried out similarly with glycine-HCl buffer solution at pH 5.0 and 40 µL, of HRP (20 U/mL). The entrapment of ASP within alumina (0.03%) was carried out similarly with glycine-NaOH buffer solution (pH 8.5) and 40 µL, of ASP (152 U/mL). The entrapment of all enzymes was full, as indicated by lack of activity in the supernatant solutions and washings (see below).

Enzymatic Activity and Determination of Thermal Stability

AcP@alumina. After rinsing with 1.0 mL of glycine solution (pH 4.5), the bioactive hybrid was left for incubation at 37° C. for 30 min. Then, the rinsing solution was replaced with 1.0 mL of 10.8 mM of the substrate (pNPP) in glycine—HCl buffer solution (pH 4.5), and the enzymatic activity was measured by following the formation of p-nitrophenolate (pNP, FIG. 1-1) spectroscopically through the absorption at 405 nm, at temperatures ranging from 30 to 75° C. Readings were taken every 20 sec for 30 min. The rinsing solution was also tested for enzymatic activity by the transfer of 500 µL of the solutions into cuvettes and adding 1.0 mL of 10.8 mM of substrate (pNPP) solution. The dose—response kinetics of the composites was measured by using different pNPP concentrations. The rates for the enzymatic reaction were calculated according to regular pseudo-first order kinetics and the Michaelis-Menten equations. For comparative analysis of free AcP, 1 µl (780 U/ml) in 1.0 mL glycine solution (pH 4.5) was taken and reacted similarly to the entrapped enzyme.

Figure 9:
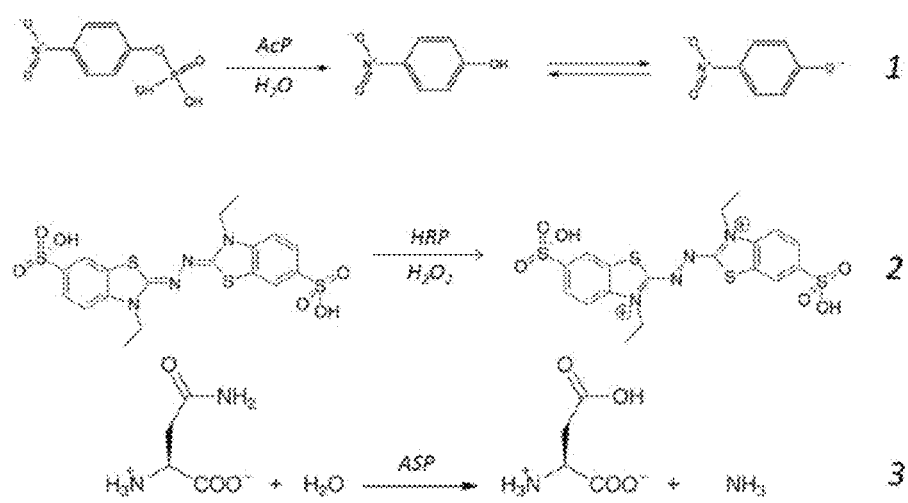
FIG. 9 exemplifies the enzyme-catalyzed chemical reactions used.

HRP@Alumina. The enzymatic activities of free and entrapped HRP were determined using ABTS as the reducing substrate (FIG. 9). The assay system was a mixture of 1.0 mL of 0.5 mM ABTS and 0.2 mL of 30% H2O2 in 2.0 mL of 50 mM glycine-HCl buffer (pH 5.0). The enzymatic activity was measured spectrophotometrically as a rise in absorbance of the formation of the oxidized ABTS at 425 nm. To polystyrene cuvettes containing HRP@alumina in 1.0 mL glycine solution (pH 5.0) was added, and comparative incubation was carried out at 37° C. and 75° C. for 1 h. The rinsing solution of HRP@alumina sample was also tested for enzymatic activity by the transfer of 500 µL of the solutions into cuvettes and adding 1.0 mL of 0.5 mM ABTS and 0.2 mL of 0.2 mM $H_2O_2$ in 2 mL of 50 mM glycine-HCl buffer (pH 5.0). The activity of HRP was determined by following the formation of oxidized ABTS forming during the first 10 min of the reaction.

Figure 10A:
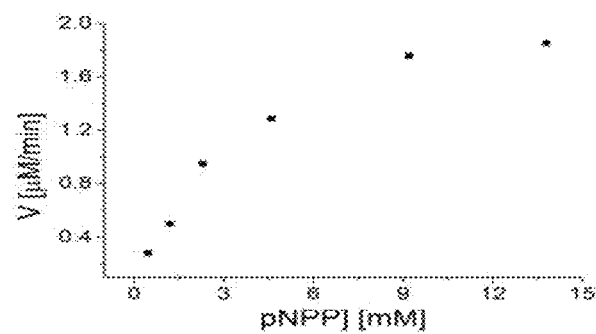
FIGS. 10A-C demonstrates dose-response curves of AcP@aluminap.
Figure 10B:
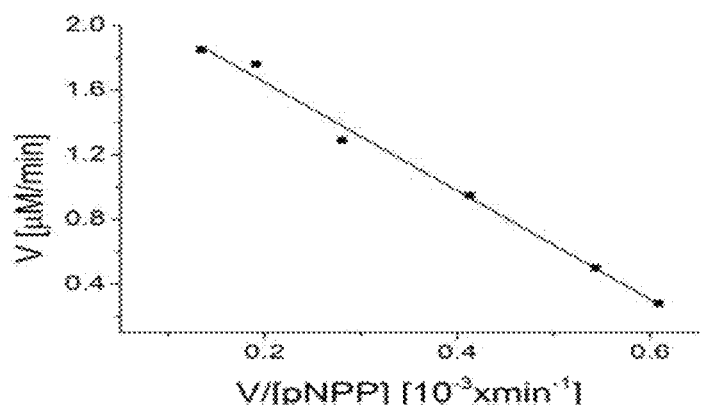
Figure 10C:
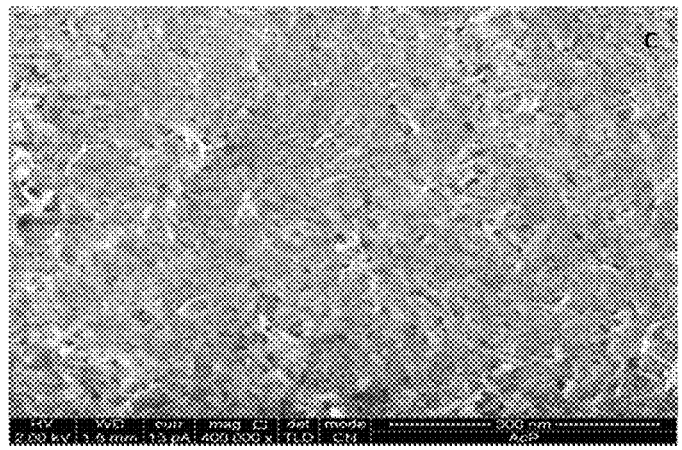

ASP@Alumina. The activity was measured using Nessler's reagent (FIG. 10). The reaction mixture was of a final volume of 3.0 mL containing 50 mM glycine-NaOH buffer (pH 8.5) and 189 mM L-asparagine. This was placed in either the final polystyrene cuvette containing the ASP@alumina or added to 0.4 µL (152 U/mL) enzyme solution. Both of cuvettes were kept under 1.0 mL glycine-NaOH solution at pH 8.5 during incubation at 37° C. and 75° C. for 1 h. The rinsing solution of the ASP@alumina was also tested for enzymatic activity by the transfer of 500 µL of the solutions into cuvettes and adding 50 mM glycine-NaOH buffer (pH 8.5), 189 mM L-asparagine. The reaction was stopped by adding 100 µL of 1.5 M trichloroacetic acid. The solution was centrifuged followed by adding 1 mL of Nessler's reagent to 1 mL of the supernatant. The absorbance at 436 nm of the resulting solution gave a measure of enzyme activity. A standard curve was prepared with ammonium sulfate and the activity of ASP was determined by following the ammonia formation during 30 min of the reaction.

Testing the Free Enzymes. To compensate for the slower reactivity of the entrapped enzymes, lower concentrations of the free enzymes were taken—×4 smaller for AcP, and ×10 smaller for the other two enzymes.

Characterization Techniques

The crystal phase and crystallinity of the samples have been studied by X-ray diffraction method (Bruker D8 Advance) using Cu-Kα irradiation ($\lambda$=1.54 Å), samples being scanned along 2θ in the range of 4-75° at a speed of 0.5 degrees per minute. The spectral analysis of enzymatic activity was carried out using HP 8453 Diode Array spectrophotometer. For scanning electron microscopy (SEM, ultrahigh resolution Magellan 400 L electron microscope), the final suspension of the entrapped enzyme was coated on silicon wafer and fully dried under vacuum. DSC curves were obtained with 204 F1 Phoenix NETZSCH apparatus and a heating rate of 10° C. $min^{-1}$ was used from 30° C. to 150° C. under nitrogen. CD spectra were recorded on a J-810 Jasco spectropolarimeter. The measurements of solutions were taken using a 2-mm path length cuvette and coated slides were used for the entrapped proteins at 20° C. Thermal stability studies were performed between 20 and 90° C., at a constant heating rate of 3° C./min.

Results and Discussion

The Enzymatic Activity and Thermal Stability of Acid-Phosphatase Entrapped in alumina (AcP@alumina)

Figure 11A:
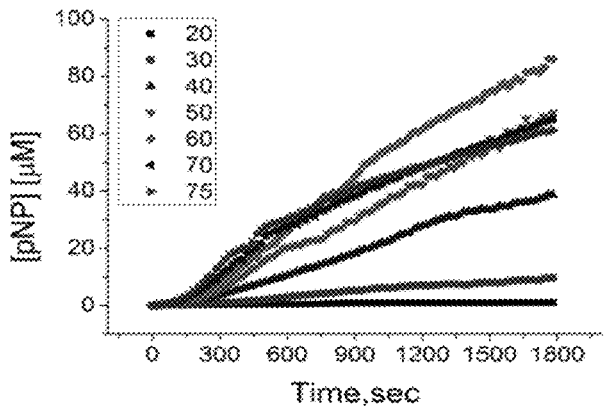
FIGS. 11A-B show
Figure 11B:
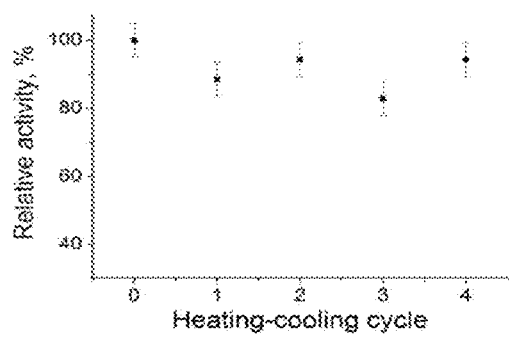

FIG. 11 shows the activity of the entrapped enzyme as a function of the substrate concentration. The activity observed was from the entrapped enzyme only: rinsing solutions have been analyzed and their activity was found to be negligible, and in fact even lower than simple non-enzymatic hydrolysis. For instance, while AcP@alumina reaches a rate of 0.351 mM/min after 10 min at 30° C., the activities of the washing solution and of non-enzymatic hydrolysis were 0.011 and 0.014 mM/min, respectively; similar observations characterize the two other enzyme entrapments in this report. Analysis of the data of FIG. 11A with an Eadie-Hofstee plot (FIG. 11B) provides Michaelis-Menten (MM) parameters of Vmax=2.3 mM/min and Km=3.38 mmol Km of free AcP in glycine buffer solution is 1.25 mmol, and the difference between the two Km values is a reflection of the diffusional difficulties that the porous alumina matrix imposes on the substrate molecules. Yet the fact that the graph is perfectly linear implies that the MM mechanism is obeyed, which in turn implies that the distribution of the enzyme molecules is homogeneous within the matrix, and that there is no denaturation of the entrapped enzyme: such denaturation leads usually to a distribution of activities (relating to the distribution of the strength of the denaturation), which in turn leads to non-compliance with the MM mechanism. The activity is possible at all because of the porosity of the matrix. the crystalline nanorods (about 1×10 nm) morphology was densely packed. The mesopores from few to more than 20 nm were also observed. Similar morphologies were obtained for HRP@alumina and ASP @ alumina.

In solution the typical thermal behavior of AcP was characterized by the expected gradual decrease of activity at temperatures above 400° C., coming to a full stop of activity at temperatures exceeding 70° C.; and it should be noted that for adsorbed AcP on Ca-polygalacturonate the thermal stability was even worse. In accordance with the present technology, the stability of alumina-entrapped AcP was found to be so high that its activity increased with temperature up to 60° C. (!). Decrease in activity began beyond that temperature, but still, the activity at the highest temperature measured, 750° C., was higher than at room temperature by about two orders of magnitude. Furthermore, another manifestation of the thermal stability of the entrapped AcP was its stability to prolonged cycle periods of heating to 60° C. and cooling.

Figure 12A:
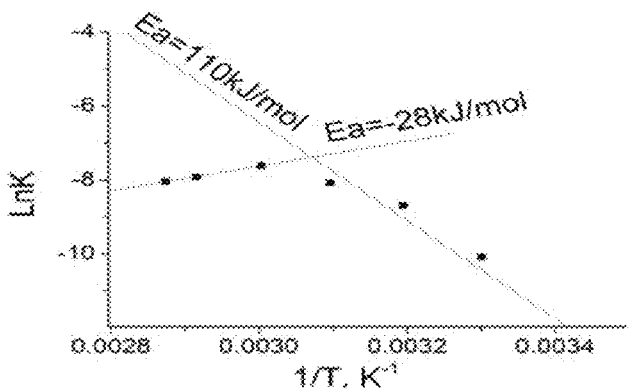
FIGS. 12A-B provide Arrhenius plot for the pNPP hydrolysis catalyzed by entrapped FIG. 12A and free FIG. 12B AcP.
Figure 12B:
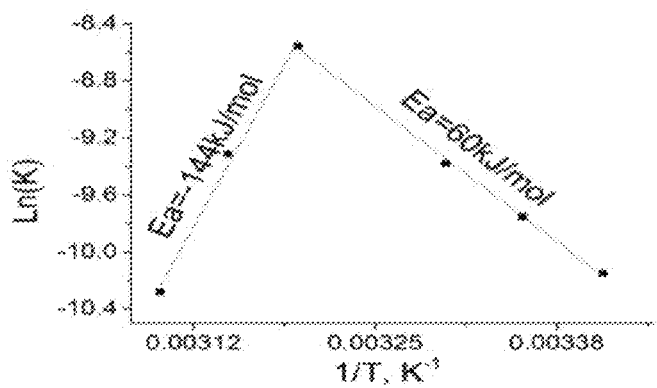

As the enzymatic hydrolysis of pNPP was pseudo-first-order (water is in excess), the temperature dependence of the rate constant is describable by Arrhenius'law, $k=A \cdot e^{-E_a/RT}$, (where k is the rate constant, Ea the activation energy, T the temperature, R the gas constant and A is the Arrhenius pre-factor). The data in FIG. 12A was thus subjected to an Arrhenius analysis, and the results are shown in FIG. 12A. Two quite different slopes are seen: the negative slope corresponds to (positive) activation energy of the pNPP hydrolysis reaction of 110 kJ/mol; that is, up to 60° C. the classical increase of activity with temperature is observed. Then there is the positive slope with an apparent negative activation energy of −28 kJ/mol, which represents the temperature range where denaturation occurs, that is, where the activity of the enzyme is disrupted by the heating. In solution (FIG. 12B) the enzymatic reaction activation energy (measured over a temperature range of 20-50° C.) was lower—60 kJ/mol—and attributed to the higher value for the entrapped to diffusional restrictions of the pNPP inside the micropores network, until the enzyme was reached. Note also that the slope representing the denaturation process was much steeper in solution with apparent negative activation energy of −144 kJ/mol. This then is the trade-off: a very high thermal stability, but lower reaction rates. For many applications, thermal stability of the enzyme is the more important feature.

Finally, the Arrhenius pre-factors, A, of the free and entrapped enzymes were measured. $A=Z\rho$, where Z is the frequency of collisions of the substrate molecule with its reactivity target, and $\rho$ is the orientation parameter (usually less than unity). For the entrapped enzyme the prefactor value is $A=3.54.10^{14}$ sec$^{-1}$, and this value is six orders of magnitude higher (!) than that of the free enzyme: $4.34.10^8$ sec$^{-1}$. To understand this large difference, it should be noted that the perfect linear compliance to the Arrehnius equation indicates that the rate determining step is the enzymatic reaction. Therefore a plausible explanation for the very high A value in the entrapped case is a dramatic increase in the number of collisions within nanopore that leads to the active site and the substrate that resides near it. Furthermore, this high value probably also reflects a favorable orientation of the pNPP molecules for fruitful collisions with the active site, that is, that the nanopore acts as an orientation-directing restriction. In other words, in the nanopores, although though initial encounters are lower than in the solution, once the reactants meet the enzyme, they get trapped to provide a large number of collisions before escaping the cage.

Figure 13A:
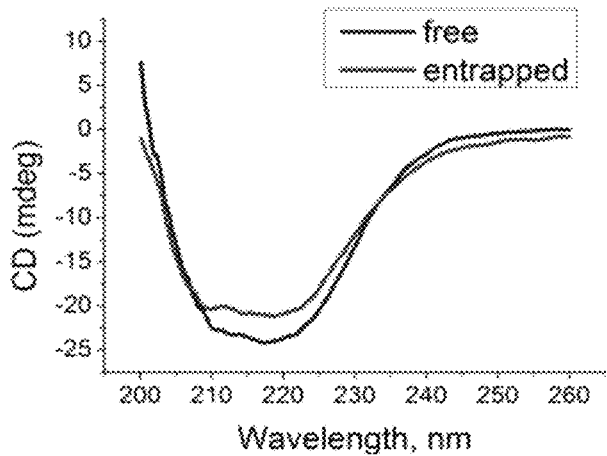
FIGS. 13A-B provide FIG. 13A Circular dichroism spectra of AcP in a freshly made solution and of AcP entrapped within alumina.
Figure 13B:
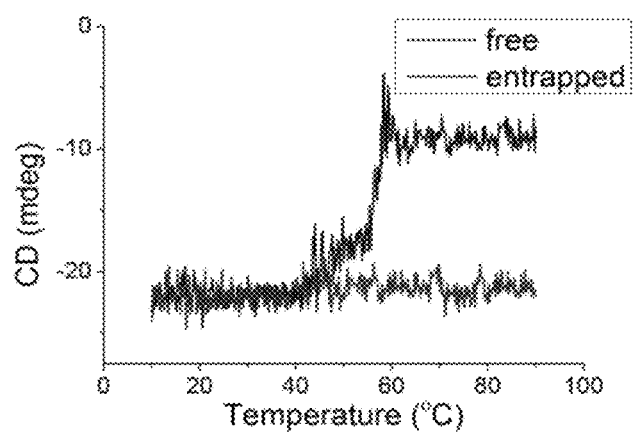

These observations can be interpreted by using protein dynamics considerations within nanopores. It is known that silica sol-gel entrapped proteins are essentially immobile within the matrix, consistent with interactions between the matrix surface functional groups and the protein surface functional groups, causing motion restriction. It suggests that the amorphous ceramic matrix is likely templated around the protein, leading to the restricted mobility. In this context, it was shown that entrapment results in only little perturbation of the tertiary and quaternary conformation of the protein. The exceptional thermal stability and dramatic increase in the number of collisions within nanopore in the present case of entrapment within alumina, leads one to suggest that the rotational mobility of enzyme within alumina is restricted even to a higher degree than in silica, providing the needed conditions for thermodynamic stability. This observation can be related to the crystalline nature of the alumina matrix. Amorphous silica is relatively soft compared to alumina, and during the heating the structure can still rearrange, providing more freedom leading eventually to earlier unfolding. The dense structure of crystalline boehmite nanorods of alumina keeps enzymes tighter, preventing easy unfolding. Two additional measurements were employed to investigate the thermal stability. The first of these is comparative circular dichroism (CD) follow-up. Since the CD spectrum is sensitive to conformational changes and is a common spectroscopic method for studying enzyme structure, one can use this tool for detection of denaturation as well. As seen in FIG. 13A, the CD spectra of the free and entrapped enzyme are quite similar, indicating the (non-trivial result) that the conformation of enzyme remains intact upon entrapment. The free and entrapped enzymes were then heated from 10 to 90° C. at a rate of 3° C./min, and the ellipticity at the characteristic helical value of 215 nm was monitored (FIG. 13B). It is clearly evident that while the free enzyme undergoes conformational changes above 40° C. (the ellipticity drops) in the case of the entrapped enzyme, the ellipticity remains constant in the interval 20-90° C.

Figure 14:
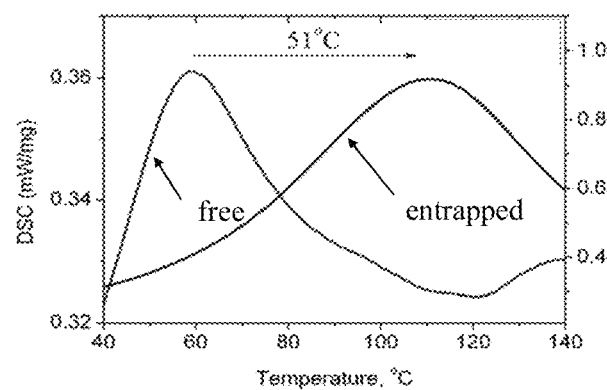
FIG. 14 provides DSC analysis of free and entrapped acid phosphatase. An increase of 51° C. in the denaturation temperature is observed for AcP@alumina (right curve), compared with free AcP (left curve).

Yet another proof of the enhanced thermal stability comes from differential scanning calorimetry (DSC) analysis. The result of this analysis, which was developed for the above detailed entrapped protein stability indicator, follows the changes in the denaturation temperature upon entrapment. Extremely high stabilization is seen in FIG. 14: The denaturation temperature is shifted by 51° C. higher. This observation is in agreement with the CD spectra and kinetic measurements analyses.

The Thermal Stability of Horse-Reddish Peroxidase and Asparaginase Entrapped in Alumina (HRP@Alumina and ASP@Alumina)

While AcP was the subject of the detailed study, it was important to learn if the exceptional thermal stability induced by the alumina matrix was a general phenomenon which holds also for other enzymes and HRP and ASP were selected for that purpose. In FIG. 15A, the activity of free HRP is compared to the activity HRP@alumina after incubation for one hour at two temperatures, 37 and 75° C. Whereas for the free HRP the drop in activity was a factor of 90, to less than 1.2% of the original activity, for the entrapped enzyme the reduction is only by a factor of 1.5, to 65% of the original activity. DSC analysis (FIG. 15B)

showed that the denaturation temperature of HRP is shifted to a higher temperature by 30° C. when entrapped within the alumina matrix.

As was the case with AcP@alumina, the CD spectra of the free and entrapped HRP are quite similar (FIG. 16A), indicating that the conformation of enzyme remains intact upon entrapment. The difference between the minima in the CD spectra—205 and 210 nm for the free and entrapped enzyme is related to the change in environment from water to alumina. The free and entrapped enzyme were then heated from 20 to 90° C. at a rate of 30 C/min, and the ellipticity at the characteristic helical value of 205 nm was monitored (FIG. 16B). It is clearly evident that while the free enzyme underwent conformational changes above 65° C. (the ellipticity drops) in the case of the entrapped enzyme, the ellipticity remained constant in the interval 20-90° C.

Figures 17A, 17B:
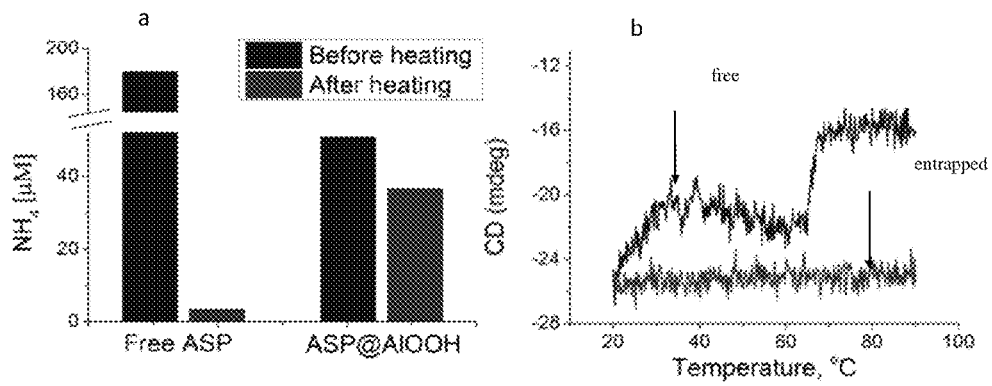
FIGS. 17A-B provide
Figure 18:
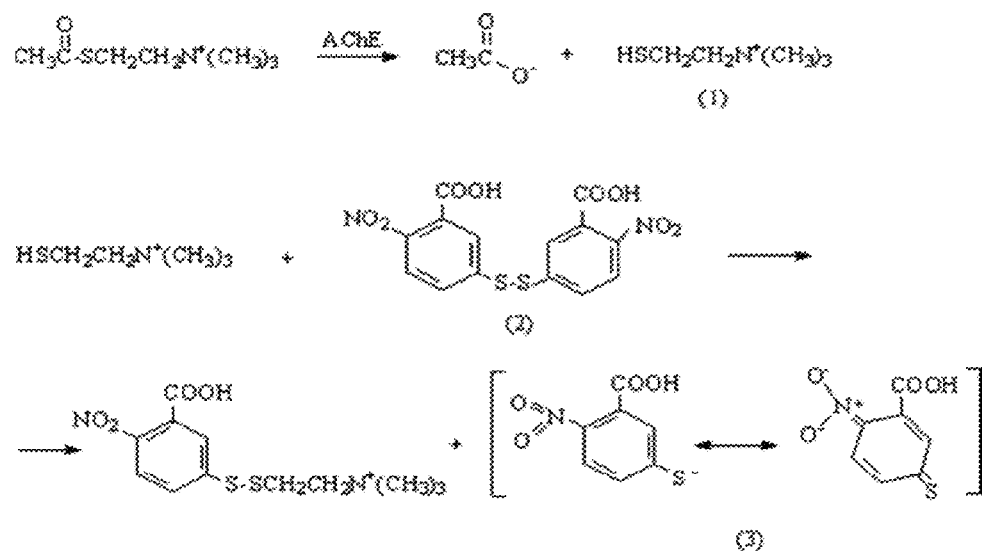
FIG. 18 exemplifies AChE catalyzed hydrolysis of acetylthiocholine and thiocholine (1) reaction with Ellman reagent (2) with yellow anion (3) production.
Figure 19:
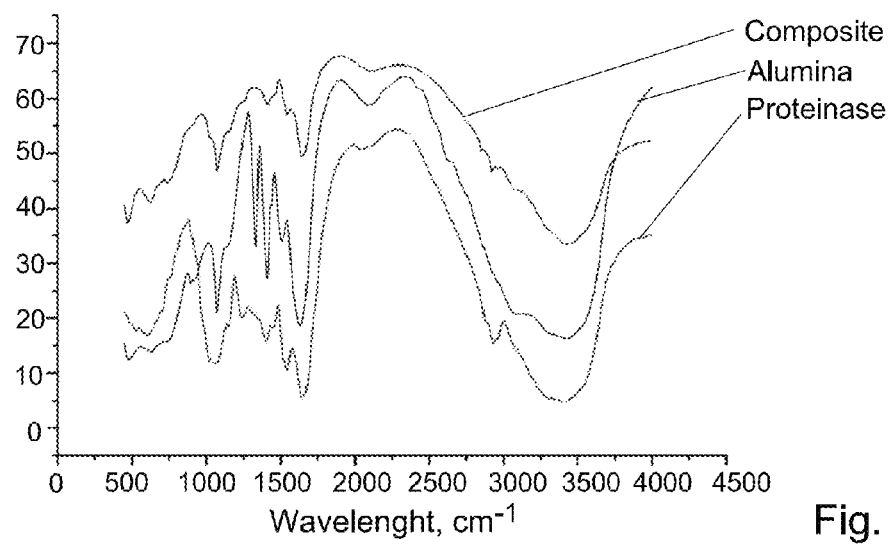
FIG. 19 provides FTIR spectra of the pure alumina, proteinase and composite.

Similar tests performed on ASP@alumina support the notion that entrapment in boehmite alumina provides major thermal stability. FIG. 16 follows both the activity parameter and the CD-spectral parameter, and it is seen that the thermal stability observed for AcP and for HRP is a feature of ASP as well: the activity (FIG. 17A) of free ASP the drop in activity upon heating by a factor of 51, to less than 1.9% of the original value, whereas for the entrapped enzyme the reduction is only by a factor of 1.4, to 72% of the original activity. The change in ellipticity due to heating the free and the entrapped ASP shows the similar stability behavior as for HRP. The ASP unfolding was monitored at 220 nm where the spectral changes were largest (FIG. 17B): It is seen that while free ASP undergoes conformational changes sharply above 65° C., the ellipticity of entrapped ASP remains practically constant in the interval 20-90° C.

Three More Enzymes—Enzymes of Industrial Importance

The xylanase (XLNS), proteinase (PRTNS) are traditional representatives of industrial enzymes. Xylanase is the hydrolytic enzyme involved in depolymerization of xylan, finds application in many industrial processes such as enzymatic bleaching of paper pulp, juice clarification, extraction of oils from plants, texture improvement in bakery, bioconversion of agricultural wastes, bioscouring in textiles and improving digestibility of animal feed. Proteinases (PRTNS) represent one of the three largest groups of industrial enzymes and find application in detergents, leather industry, food industry, pharmaceutical industry and bioremediation processes. Acetylcholinesterase (AChE) is used in a variety of chemical warfare applications, and is also a therapeutic enzyme.

XLNS, PRTNS AChE were entrapped within alumina by adding the enzyme during the sol-gel manufacturing process. Using kinetics, DSC and CD analyses, it is demonstrated that the alumina matrix not only protects form thermal denaturing but that over a certain temperatures range, it enhances quite significantly the activity of the enzymes. Even extremely high temperature treatment (>100° C.) does not lead to denaturation of entrapped protein. XLNS@alumina showed activity after the treatment at 105° C. during 10 min comparing with as-made sample, the treated remained 71% (!) of initial activity. It has also been showed that the stability of entrapped enzymes was not limited by temperature, but also from the chemicals: after treatment with inhibitor of free AChE the drop in activity was near of a factor of 3000(!), to less than 0.04% of the original activity, for the entrapped enzyme we observed even minor increasing in the activity.

For the entrapment of PRTNS, a mixture of 50 µL of glycine-NaOH buffer solution (pH 7.5) and 200 µL of freshly prepared alumina sol was transferred to a cuvette and then 20 µL of PRTNS (15 U/mL) was added. Ten minutes later the sol was left in vacuum desiccator at room temperature for 24 hours. The PRTNS@alumina was rinsed inside final polystyrene cuvette with 1.0 mL of glycine solution (pH 7.5) to assure removal of any adsorbed protein. The entrapment of XLNS within alumina was carried out similarly with glycine-HCl buffer solution at pH 4.5 and 20 µL of XLNS (30 U/mL). The entrapment of all enzymes was full, as indicated by lack of activity in the supernatant solutions and washings.

For the entrapment of AChE, a 150 µL of freshly prepared alumina sol was transferred to a cuvette and then 50 µL of AChE (500 U/mg) was added. Ten minutes later the sol was left in vacuum desiccator at room temperature for 24 hours. The AChE@alumina was rinsed inside final polystyrene cuvette with 2.0 mL of TDW to assure removal of any adsorbed protein. The entrapment of enzyme was full, as indicated by lack of activity in the supernatant solution and washing.

Enzymatic Activity and Determination of Thermal Stability:

PRTNS@alumina. After rinsing with 1.0 mL of glycine solution (pH 7.5), the bioactive hybrid was left for incubation at 37° C. for 30 min. Then, the rinsing solution was replaced with 2.0 mL of 1% weight/volume casein solution (prepared by mixing 1 mg/ml of casein in the 50 mM potassium phosphate buffer), 0.5 ml of Folin's reagent with following vortexing and the enzymatic activity was measured by following the formation of free tyrosine interacting with Folin's reagent by producing a blue colored chromophore measured as an absorbance value spectroscopically through the absorption at 660 nm, at temperatures ranging from 30 to 70° C. Absorbance values generated by the activity of the enzyme are compared to a standard curve, which is generated by reacting known quantities of tyrosine with the Folin's reagent to correlate changes in absorbance with the amount of tyrosine in micromoles. The rinsing solution was also tested for enzymatic activity by the transfer of 2.0 mL of casein solution and 0.5 ml of Folin's reagent. For comparative analysis of free PRTNS, 2 µl (15 U/ml) in 1.0 mL glycine solution (pH 7.5) was taken and reacted similarly to the entrapped enzyme.

XLNS@Alumina. The enzymatic activities of free and entrapped XLNS were determined using xylan as the substrate. The assay system was as a mixture of 2.0 mL of 1% (w/v) xylan solution (prepared by mixing 1 mg/ml of xylan in the glycine-HCl buffer solution at pH 4.5) and 0.1 ml of 0.04M DNSA solution. Xylanase hydrolyzes the polymer xylan into the xylose monomers. The free xylose units produced as a result of xylanase activity react with DNSA reagent and form a colored complex that is measured by spectrophotometer at wavelength 540 nm. The enzymatic activity was measured spectrophotometrically as a rise in absorbance. Absorbance values generated by the activity of the enzyme are compared to a standard curve, which is generated by reacting known quantities of xylose with the DNSA reagent. To polystyrene cuvettes containing XLNS@alumina in 1.0 mL glycine solution (pH 4.5) was added, and comparative incubation was carried out at 37° C. for 1 h. The rinsing solution of XLNS@alumina sample was also tested for enzymatic activity by the transfer of 500 µL of the solutions into cuvettes and adding 2.0 mL of 1% (w/v) xylan solution and 0.1 ml of 0.04M DNSA solution. The activity of XLNS was determined by following the formation of reducing sugars.

AChE@Alumina. After rinsing with 2.0 mL of TDW, the bioactive hybrid was left for incubation at 37° C. for 30 min. Then, the rinsing solution was replaced with 3 mL of TDW, 20.0 µl of 0.075M acetylthiocholine iodide and 100 µl of 0.01M dithiobisnitrobenzoic acid. The blank consisted of TDW, substrate, and DTNB solutions. The enzymatic activity was measured by following the formation of yellow anion spectroscopically through the absorption at 412 nm, at room temperature. The rinsing solution was also tested for enzymatic activity by the transfer of 1 mL of the solution into cuvette and adding 3 mL of TDW, 20.0 µl of the substrate and 100 µl of 0.01M DTNB. For comparative analysis of free AChE, 5 µl (500 U/mg) was taken and reacted similarly to the entrapped enzyme. For the test with inhibitor the aluminium chloride solution was taken. The 10 µl of 0.24M AlCl3 solution was added to the cuvettes with free and entrapped AChE before adding of substrate and kept during 5 min.

Testing the Free Enzymes. To compensate for the slower reactivity of the entrapped enzymes, lower concentrations of the free enzymes were taken—×10 smaller all: XLNS, PRTNS and AChE enzymes.

Characterization Techniques:

The obtained samples were characterized by IR spectroscopy on <<Perkin Elmer Frontier FT-IR>>. Specific surface areas, pore volumes and pore sizes distribution have been determined using the nitrogen adsorption-desorption method at 77 K (Micromeritics ASAP 2020). Surface areas were calculated using the BET equation. Pore volumes and pore size distributions were calculated using the BJH method. Before the analysis the sample was degassed over night at room temperature. For scanning electron microscopy (SEM, ultrahigh resolution Magellan 400 L electron microscope), the final suspension of the entrapped enzyme was coated on silicon wafer and fully dried under vacuum. The spectral analysis of enzymatic activity was carried out using HP 8453 Diode Array spectrophotometer. DSC curves were obtained with 204 F1 Phoenix NETZSCH apparatus and a heating rate of 10° C. min$^{-1}$ was used from 30° C. to 150° C. under nitrogen. CD spectra were recorded on a Spectropolarimeter J-810 (Jasco Corporation). The measurements of solutions were taken using a 2-mm path length cuvette and coated slides were used for the entrapped proteins at 20° C. Thermal stability studies were performed between 20 and 90° C., at a constant heating rate of 3° C./min.

Individual components (proteinase and alumina) and also the composite prepared by entrapment of PRTNS within alumina matrix were studied by FTIR analysis. The assignment of absorption bands in spectra was performed according to the literature data. The results clearly show a superposition of the typical absorptions bands of the matrix and the dopant. The main absorption bands of boehmite correspond to the following vibrations at the regions 400-830 cm$^{-1}$ and 1050-1070 cm$^{-1}$ related with Al—O—H vibrations. A wide band in the region of 3000-3600 cm$^{-1}$ reveals the presence of non-equivalent water molecules, hydroxo groups and hydrogen bonds. However, the main difference of alumina and proteinase is the emergence of I and II amide bands revealing the presence of the protein. The amide bands resulted from bending vibrations of the N—H/C—N bonds appears in the region of 1510-1600 cm$^{-1}$.

Figure 20A:
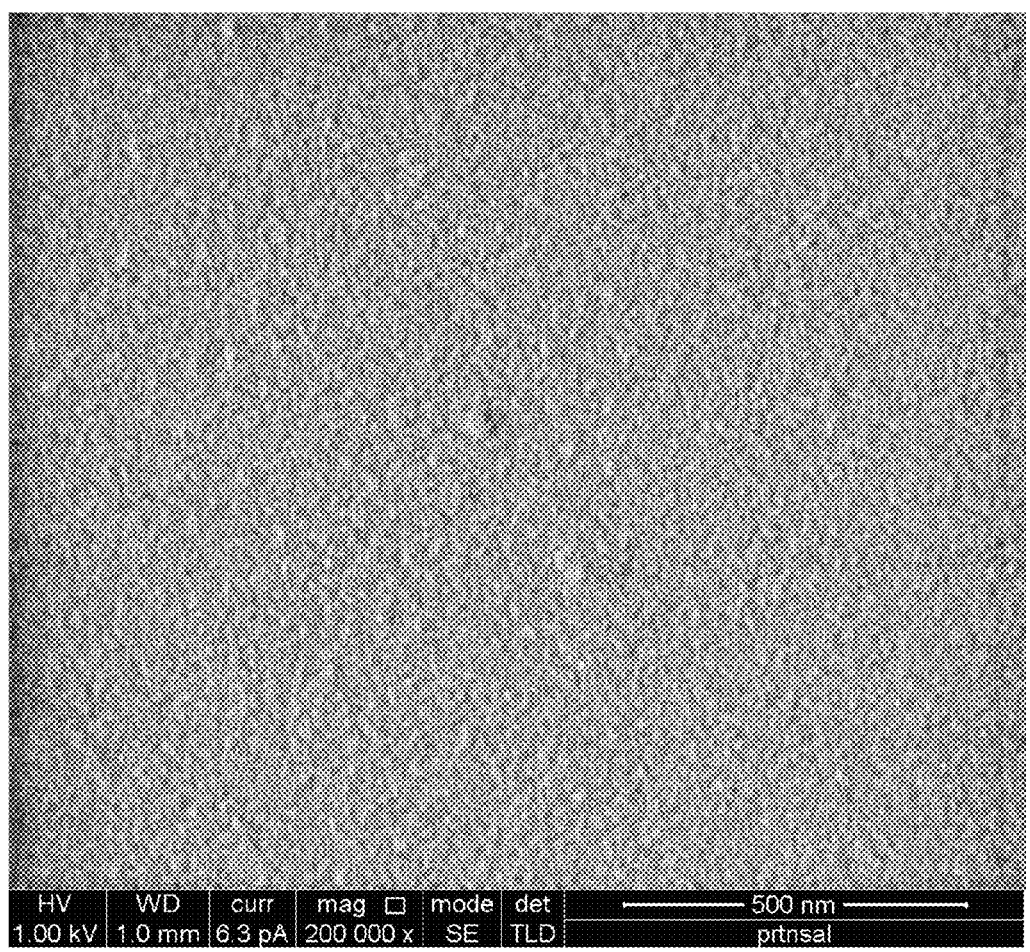

FIG. 20 shows the morphology of the final PRTNS@alumina composite, which are densely packed. Similar morphology was obtained for XLNS@alumina.

Surface area and porosity analyses (by nitrogen adsorption, analyzed by the BET and BJH equations) confirmed with typical micro-mesoporosity (FIG. 20). For the composite prepared by entrapment of PRTNS—the values were: surface area of 174 m$^2$/gr, pore volume of 0.116 cm$^3$/gr and pore size of ~3.5 nm. It needs to be assumed here that the protein release from alumina matrix strongly depends on proteins size and average pore size of matrix. In this case, maximum of proteinase release which was reached during 25 hours is only 7%. Similar behavior was observed for xylanase entrapped in alumina: there is a plato of 4% release at 15 hours.

Figure 21C:
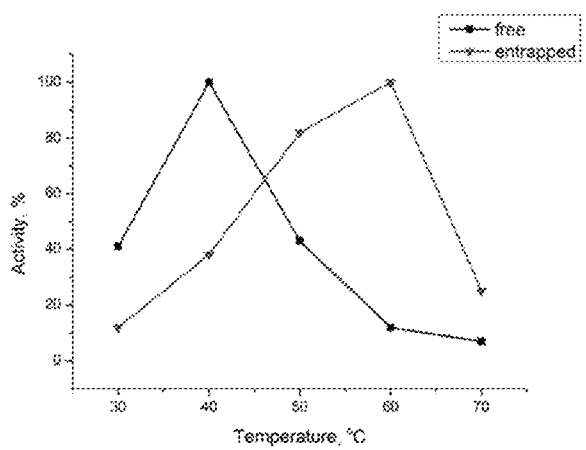
Figure 21D:
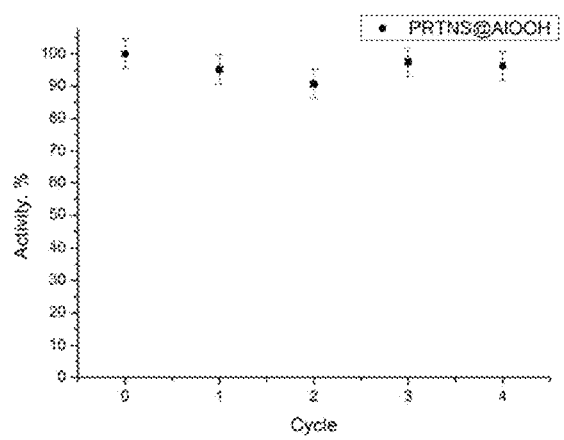

In solution the typical thermal behavior of PRTNS is characterized by the expected gradual decrease of activity at temperatures above 40° C., coming to a full stop of activity at temperatures exceeding 70° C. (FIG. 21A). Similarly to the case of the theraputic enzymes, the stability of alumina-entrapped PRTNS was found to be so high that its activity increases with temperature up to 60° C. (!) (FIG. 21B). Decrease in activity begins beyond that temperature. Furthermore, another manifestation of the thermal stability of the entrapped PRTNS is its stability to prolonged cycle periods of heating to 60° C. and cooling (FIG. 21D). Taking into account that proteinases are used in many hard and harsh areas of industry this fact is even more important for practical application.

Figure 22A:
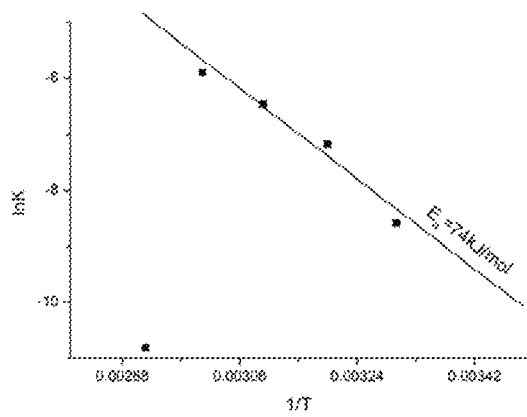
FIGS. 22A-C show FIG. 22A-Arrhenius plot for the casein decomposition catalyzed by entrapped PRTNS. There is a temperature switch points ($\approx 60°$ C.), above which the apparent activation energy becomes negative.

As the enzymatic decomposition of casein is the first-order, the temperature dependence of the rate constant is describable by Arrhenius' law, k=A·e$^{-E_a/RT}$, (where k is the rate constant, Ea is the activation energy, T is the temperature, R is the gas constant and A is the Arrhenius pre-factor). The data in FIG. 21 was thus subjected to an Arrhenius analysis, and the results are shown in FIG. 22. The negative slope corresponds to a activation energy of the casein decomposition reaction of 74 kJ/mol; that is, up to 60° C. we have the classical increase of activity with temperature. Then there is the positive slope with an apparent negative activation energy, which represents the temperature range where denaturation occurs, that is, the activity of the enzyme is disrupted by the heating. In solution the enzymatic reaction activation energy is lower—43 kJ/mol—and it is attributed to the higher value for the entrapped to diffusional restrictions of the big molecules of casein inside the mesoporous network, until the enzyme is reached. For many industrial applications, thermal stability of the enzyme is the more important feature.

Figure 22B:
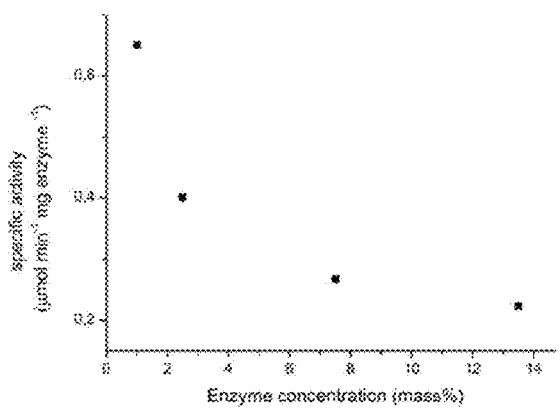
Figure 22C:
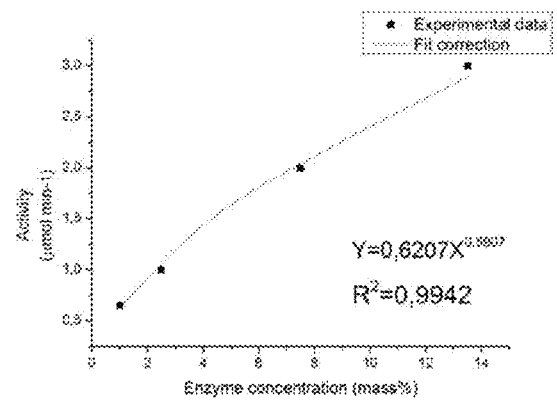

FIG. 22B shows that specific activity of the entrapped PRTNS and that it depends on the extent of doping of alumina by the enzyme. The decrease in specific activity as the enzyme concentration in the monolith increases can be caused by aggregation or denaturation of the enzyme in matrix. It may be also a consequence of a small decrease in accessibility of the enzyme to the substrate as the enzyme concentration increases. Similar dependence of activity on concentration has been reported for encapsulated trypsin. To evaluate effect of aggregation of enzyme by increasing of loading within sol-gel matrix, we offer very simple explanation (FIG. 22C). Taking account that available surface area of enzyme (S) is the function of composite activity (A) and volume of enzyme (V) is the function of concentration (C) we can conclude the following equation:

$$A \approx C^{2/3} \tag{1}$$

According the classical equation S~V⅔. So, if the exponent in the fit correction is near to ⅔ (0.67) we deal with homogenous distribution of the dopant, where practically each of the enzyme unit take part in the reaction and aggregation is absent. If this value less than 0.67 aggregation occurs. In this case exponent factor is 0.59, which means that aggregation takes place, but the value is quite close to ideal 0.67 where aggregation negligible.

Two additional measurements were employed to investigate the thermal stability. The first of these is comparative circular dichroism (CD) follow-up. Since the CD spectrum is sensitive to conformational changes and is a common spectroscopic method for studying enzyme structure, one can use this tool for detection of denaturation as well. As observed from the CD spectra of the free and entrapped enzyme are quite similar, indicating the (non-trivial result) that the conformation of enzyme remains intact upon entrapment. The free and entrapped enzymes were then heated from 20 to 90° C. at a rate of 30° C./min, and the ellipticity at the characteristic helical value of 225 nm was monitored. It is clearly evident that while the free enzyme undergoes conformational changes above 30° C. (the elipticity drops) in the case of the entrapped enzyme, the ellipticity remains constant in the interval 20-90° C. While the free enzyme changes the CD spectrum due to total denaturation in the case of the entrapped enzyme, the ellipticity remains similarly to native form.

Yet another proof of the enhanced thermal stability comes from differential scanning calorimetry (DSC) analysis. The result of this analysis, which was developed for entrapped protein stability indicator, follows the changes in the denaturation temperature upon entrapment.

Figure 23:
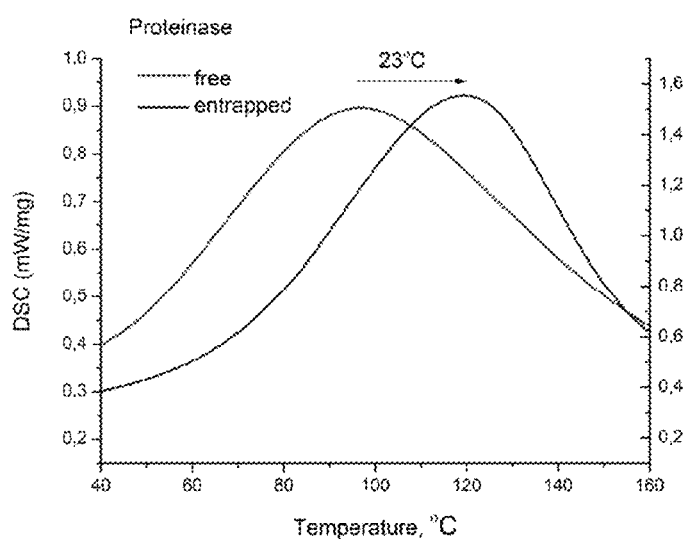
FIG. 23 provides DSC analysis: An increase of 23° C. in the denaturation temperature is observed for PRTNS@alumina (right curve), compared with free PRTNS (left curve).

DSC analysis (FIG. 23) shows that the denaturation temperature of PRTNS is shifted to a higher temperature by 23° C. when entrapped within the alumina matrix, which is in a good agreement with kinetic data.

The thermal stability of xylanase entrapped in alumina (XLNS@alumina): While PRTNS was the subject of the detailed study, it was important to check if the exceptional thermal stability induced by the alumina matrix is a general phenomenon which holds also for other enzymes—industrial in this report—and xylanase was selected for that purpose for reasons described in the Introduction.

Figure 24A:
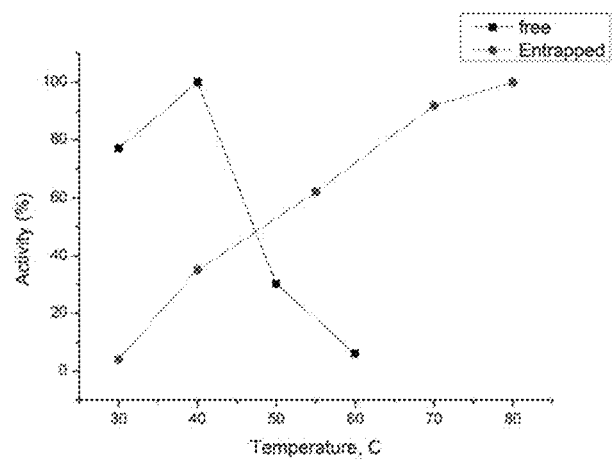
FIGS. 24A-B provide
Figure 24B:
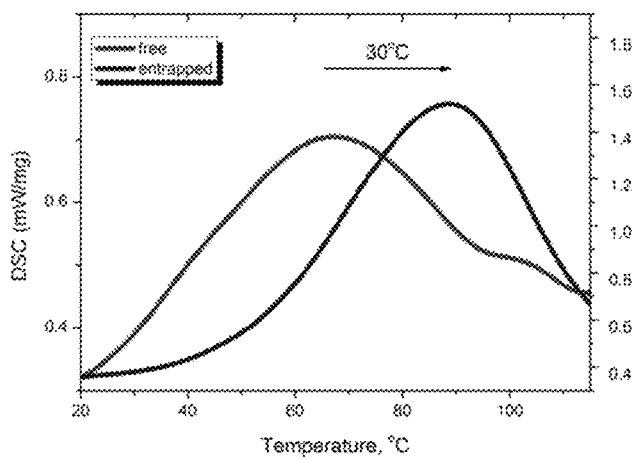

In FIG. 24A the relative activity of free XLNS is compared to the activity XLNS@alumina at different temperatures in between 30-80° C. Even stronger thermal stability was observed compared to PRTNS. Whereas for the free XLNS the activity drops after 40° C., for the entrapped enzyme the relative activity increases up to extreme 80° C. (!), where practically full list of existing enzymes loose the activity at all. DSC analysis (FIG. 24B) shows that the denaturation temperature of XLNS is shifted to a higher temperature by 30° C. when entrapped within the alumina matrix.

Figure 25A:
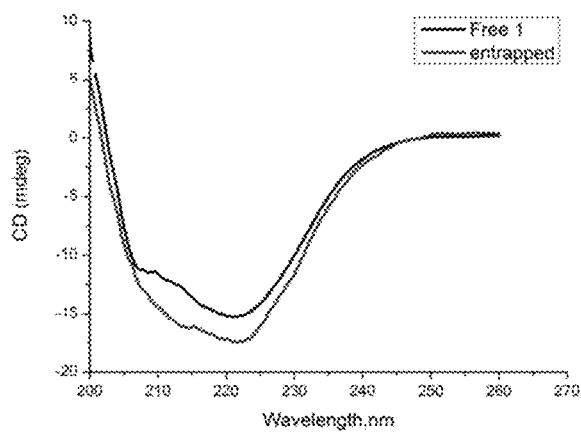
FIGS. 25A-B provides.
Figure 25B:
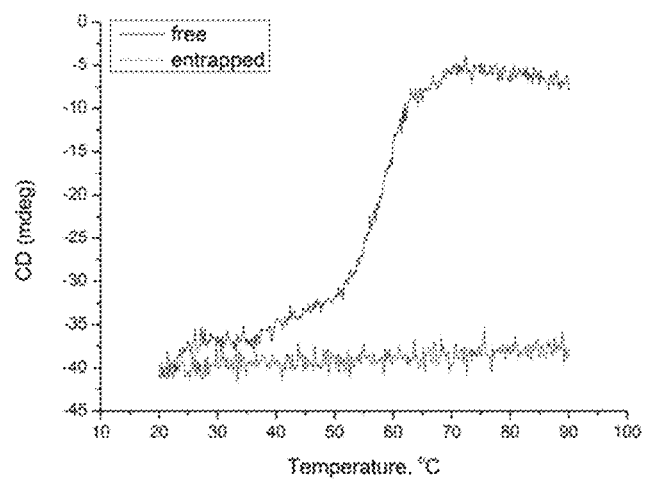
Figure 26:
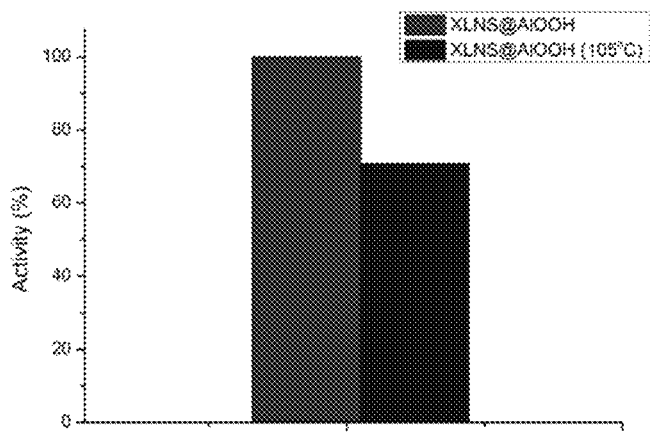
FIG. 26 shows the relative activity of as-made XLNS@alumina and after incubation at 105° C. during 10 min.
Figure 29:
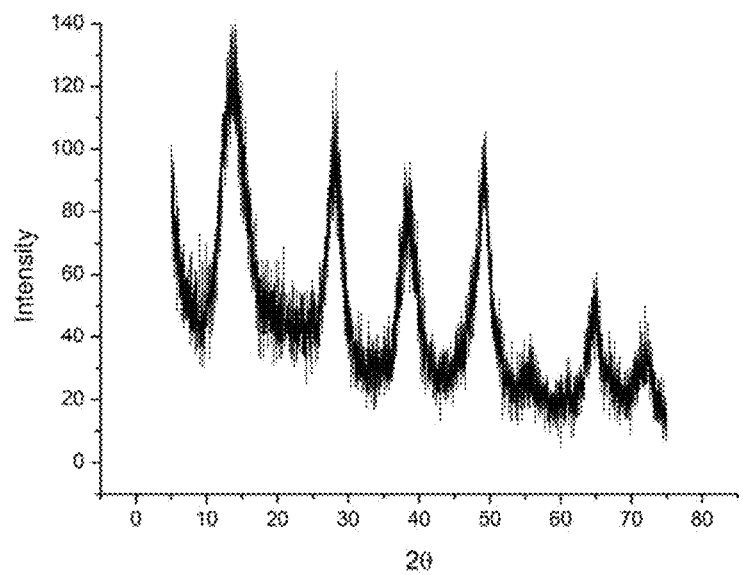

As was the case with PRTNS@alumina, the CD spectra of the free and entrapped XLNS are quite similar (FIG. 25A), indicating that the conformation of enzyme remains intact upon entrapment. The free and entrapped enzyme were then heated from 20 to 90° C. at a rate of 30° C./min, and the ellipticity at the characteristic helical value of 215 nm was monitored (FIG. 25B). It is clearly evident that while the free enzyme undergoes conformational changes above 50° C. (the elipticity drops) in the case of the entrapped enzyme, the ellipticity remains practically constant in the interval 20-90° C. Thermal unfolding of the enzyme causes precipitation in solution, as we observed during experiment, but not in the alumina glass. Both incomplete unfolding and lack of precipitation can be attributed to the influence of the alumina matrix. The enzyme molecules are relatively constrained by this matrix, which restricts the mobility of the protein molecules that is required for complete unfolding. Because the enzyme molecules are isolated in separate "cages" in porous alumina, they cannot aggregate together and precipitate. The relatively small slope (between 50-70° C.) of the plot may be an indication that the protein molecules exist in different microenvironments and have somewhat different stabilities toward unfolding.

Taking account the high thermal stability of xylanase entrapped within alumina the test of activity after sample incubation at 105° C. during 10 min was carried out. Unexpectedly, the sample showed activity and even on a high level. Comparing with as-made sample, the treated remained 71% (!) of initial activity.

The Inhibitor Stability of Acetylcholinesterase Entrapped in Alumina (AChE@Alumina):

FIG. 27A shows the activity of the free and entrapped enzyme as a function of the time. The activity of rinsing solution has been analyzed and was found to be negligible, similarly to the non-enzymatic hydrolysis. Activity of 5 µl of free AChE is much higher than for 50 µl entrapped. In FIG. 27B the activity of free AChE is compared to the activity AChE@alumina after incubation with inhibitor. Whereas for the free AChE the drop in activity was near of a factor of 3000(!), to less than 0.04% of the original activity, for the entrapped enzyme we observed even minor increasing in the activity.

Very high stability, but lower reaction rates. For mentioned application, stability of the enzyme and ability to work in presence of inhibitor are the more important features.

For the entrapment of CSP, a mixture of 0.4 mL of freshly prepared alumina sol was transferred to the quartz cuvette and then 50 µl of cisplatin 0.03M solution was added. Ten minutes later the sol was left in vacuum desiccator at room temperature for 24 hours. The CSP@alumina was covered inside final quartz cuvette with 3.0 mL of histidine buffer solution (pH 7.4) to measure the rate of drug release.

Characterization Techniques:

The obtained samples were characterized by IR spectroscopy on <<Avatar 360 FTTIR ESP>>. Specific surface areas, pore volumes and pore sizes distribution have been determined using the nitrogen adsorption-desorption method at 77 K (Quantachrome Nova 1200 series e). Surface areas were calculated using the BET equation. Pore volumes and pore size distributions were calculated using the BJH method. Before the analysis the sample was degassed for 12 hours at 80° C. The crystal phase and crystallinity of the samples have been studied by X-ray diffraction method (Bruker D8 Advance) using Cu-Kα irradiation (λ=1.54 Å), samples being scanned along 2θ in the range of 4-75° at a speed of 0.5 degrees per minute. The spectral analysis of drug release was carried out using PG instruments T 70+ UV/Vis spectrophotometer at the 203 nm with extinction coefficient 5.2 mM-1 cm$^{-1}$. Transmission electron microscopy investigations was made using Philips TECNAI G2 F20 transmission electron microscope (Roanoke, Va., USA) with an accelerating voltage of 200 kV.

Results and Discussions

FTIR—Analysis

Individual components (cisplatin, alumina) and also the composite prepared by entrapment of cisplatin within alumina matrix were studies by FTIR analysis. The assignment of absorption bands in spectra was performed according to the literature data. The results clearly show a superposition of the typical absorptions bands of the matrix and the dopant. The main absorption bands of boehmite correspond to the following vibrations at the regions 400-830 cm$^{-1}$ and 1050-1070 cm$^{-1}$ related with Al—O—H vibrations. A wide band in the region of 3000-3600 cm$^{-1}$ reveals the presence of non-equivalent water molecules, hydroxo groups and hydrogen bonds. The same absorbance can be found on the composite as well. However, the main difference of composite and boehmite is the appearance of amino band revealing the presence of the cisplatin. The absorption reveals at 1300 cm$^{-1}$ and is related with vibrations N—H band.

XRD Analysis

Next, it is important to determine the type of the alumina synthesized. Of the six crystalline phases of alumina the biologically active form of alumina used as an adjuvant in current vaccines is boehmite/pseudoboehmite. XRD analysis of alumina indicates typical boehmite structure and Scherer-equation analysis provides an elementary crystallite size of few nm (typically 3-4 nm). These results are in a good agreement with common alumina adjuvants which are also boehmite with crystallite size 4-5 nm.

N$_2$—Physisorption and TEM Study

The sample presented a narrow pore size distribution by the BJH method. The sample exhibits typical microporous isotherm, according to the IUPAC classification, associated with the presence of micropores.

The morphology of obtained samples was investigated by high resolution transmission electron microscopy. The boehmite sol-gel matrix consists of well-crystallized nanorods with average size 1×10 nm forming dense organized structure. The average pore size is about 2-3 nm, which is in a good agreement with nitrogen physisorption data.

Taking into account the global market of biomaterials with slow drug release and controlled delivery, the present work is of major applied importance. This brings to a highlight another important feature of the composites prepared by our special ultrasonic methodology: For targeted delivery of medicines, nanoparticles with the size of less than 100 nm are needed in order to overcome the biological barriers and in order to pass through capillaries. While the traditionally applied alumina-based adjuvants have size in the few microns range, the elementary building blocks of our alumina are around several tens of nm.

Cisplatin Release

Figure 30A:
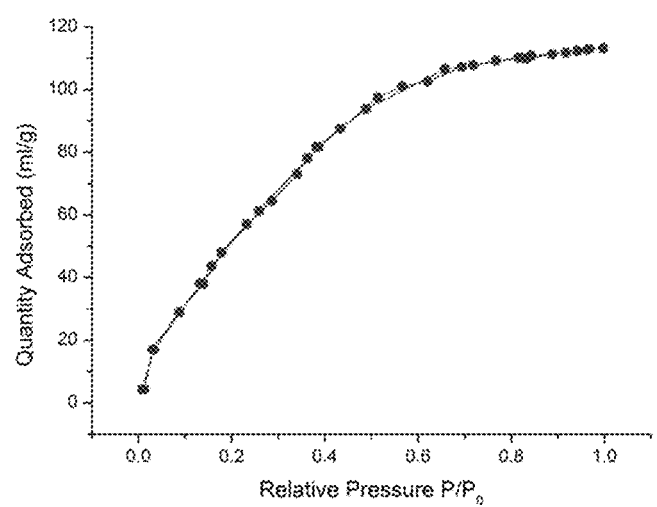
FIGS. 30A-B show short time (FIG. 30A) and long time (FIG. 30B) release profile of CSP from alumina its fit to the Weibull model.
Figure 30B:
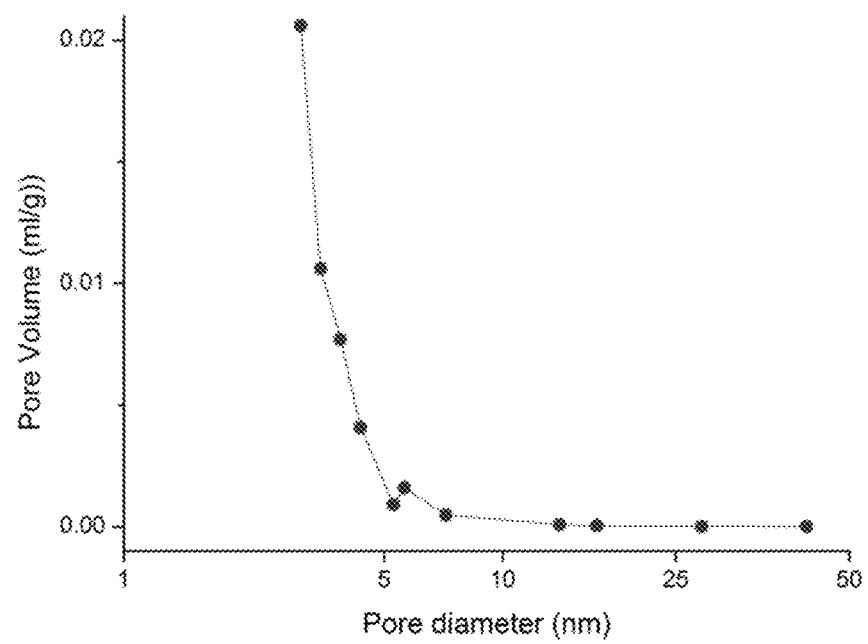

The kinetics of CSP release from the alumina into histidine buffer (pH=7.4) was measured and the results are presented in FIG. 30. It is seen that the profile of cisplatin release from alumina is represented by gradual release. This behavior was found to fit the Weibull model for both cases $$m(t) = m_\infty \cdot \left[1 - \exp\left(-\left(\frac{t}{t_c}\right)^b\right)\right]$$

Here, m(t) is the dopant fraction that is released into the extracting solvent at time t, m∞ is the total fraction that may be extracted by the chosen solvent after infinite time, tc is a characteristic time, namely the time required for 63.2% (exp(−1)) of the total extractable population be extracted, and b is a shape parameter, which may have values between 0 and 1. If b=1, the model reduces to a simple first-order model; if b<1, the curve is parabolic, with a higher initial slope (accommodating the initial 'burst' observed in some extractions). The parameter b can thus be taken as an indication of the degree of homogeneity of the extractable population: a value near to 1 implies a relatively homogeneous extractable population with tc corresponding to its first-order characteristic time, while a value far from 1 implies sample heterogeneity.

The long release kinetics of CSP was studied as a function of time during two weeks. After 12 days assay, the studying systems showed similar trends of release. During the period, alumina showed 88% release of CSP.

The invention claimed is:

1. A pharmaceutical material comprising of a plurality of alumina sol-gel particles, each particle comprising at least one labile bioactive agent.

2. The pharmaceutical material according to claim 1, wherein said bioactive agent is contained, entrapped or enclosed by said alumina sol-gel particles.

3. The pharmaceutical material according to claim 1, wherein the alumina sol gel is in a form selected from the group consisting of an amorphous material and randomly sized and shaped particles.

4. The pharmaceutical material according to claim 1, being an injectable material.

5. The pharmaceutical material according to claim 1, wherein the particles average size is from 0.1 to 50 micron.

6. The pharmaceutical material according to claim 1, wherein the labile bioactive agent is selected from the group consisting of proteins, enzymes, peptides, antibodies, nucleic acids, growth factors, cells, viruses, and carriers.

7. The pharmaceutical material according to claim 6, wherein the labile bioactive agent is selected from the group consisting of peptides, proteins, hormones, enzymes, antibodies, receptor binding proteins, antibody fragments, antibody conjugates, aptamers, iRNA, siRNA, microRNA, DNA, RNA, antisense nucleic acid, VEGF inhibitors, macrocyclic lactones, dopamine agonists, dopamine antagonists, low-molecular weight compounds, high-molecular-weight compounds, and conjugated bioactive agents.

8. The pharmaceutical material according to claim 6, wherein the labile bioactive agent is selected from the group consisting of androgen inhibitors, polysaccharides, growth factors, hormones, anti-angiogenesis factors, peptides, polypeptides, proteins, amino acids, hormones, interferons, and cytokines.

9. The pharmaceutical material according to claim 6, wherein the labile bioactive agent is one or more immunomodulators selected from a cytokine, an interleukin, interferon, colony stimulating factor, and tumor necrosis factor.

10. The pharmaceutical material according to claim 1, wherein the labile bioactive agent is selected from the group consisting of heat-sensitive, acid-sensitive, and base-sensitive bioactive agents.

11. The pharmaceutical material according to claim 10, wherein the labile bioactive agent is an enzyme, a peptide, a polypeptide, a protein, or an amino acid.

12. A pharmaceutical composition comprising a pharmaceutical material according to claim 1.

13. The composition according to claim 12, configured as a slow-release formulation, a fast-release formulation, or a sustained-release formulation.

14. The composition according to claim 12, wherein the pharmaceutical material is entrapped without spontaneous short-term or long-term release of a bioactive agent contained in the material, for maintaining or increasing the stability of a bioactive.

15. The composition according to claim 14, for prolonging shelf-life of a bioactive during storage, delivery or use, by arresting bioactive decomposition, decreasing or diminishing bioactive sensitivity, increasing or maintaining stability of a bioactive, protecting a bioactive from increased sensitivity or lability, or for achieving enhanced functionality of a bioactive.

16. A hybrid material comprising alumina sol-gel and at least one heat-sensitive bioactive material, wherein the at least one heat sensitive bioactive material is entrapped within the alumina sol-gel material and having a deactivation temperature at least 10° C. higher as compared to the same heat sensitive bioactive material when free.

* * * * *